United States Patent
Habener et al.

(10) Patent No.: US 10,137,171 B2
(45) Date of Patent: Nov. 27, 2018

(54) METHODS OF TREATMENT USING A PENTAPEPTIDE DERIVED FROM THE C-TERMINUS OF GLUCAGON-LIKE PEPTIDE 1 (GLP-1)

(71) Applicant: The General Hospital Corporation, Boston, MA (US)

(72) Inventors: Joel F. Habener, Newton Center, MA (US); Eva Tomas-Falco, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/410,703

(22) Filed: Jan. 19, 2017

(65) Prior Publication Data

US 2017/0136095 A1    May 18, 2017

Related U.S. Application Data

(63) Continuation of application No. 14/128,801, filed as application No. PCT/US2012/045537 on Jul. 5, 2012, now abandoned.

(60) Provisional application No. 61/546,698, filed on Oct. 13, 2011, provisional application No. 61/504,866, filed on Jul. 6, 2011.

(51) Int. Cl.
| | | |
|---|---|---|
| *A61K 38/26* | (2006.01) | |
| *A61K 38/08* | (2006.01) | |
| *C07K 14/605* | (2006.01) | |
| *A61K 38/00* | (2006.01) | |

(52) U.S. Cl.
CPC .............. *A61K 38/26* (2013.01); *A61K 38/08* (2013.01); *C07K 14/605* (2013.01); *A61K 38/00* (2013.01); *C07K 2319/01* (2013.01); *C07K 2319/10* (2013.01)

(58) Field of Classification Search
CPC  A61K 2300/00; A61K 38/00; A61K 47/6811; A61K 38/08; A61K 38/22; A61P 3/10
See application file for complete search history.

(56) References Cited

U.S. PATENT DOCUMENTS

| | | | |
|---|---|---|---|
| 5,574,008 | A | 11/1996 | Johnson et al. |
| 5,846,937 | A | 12/1998 | Drucker |
| 6,268,343 | B1 | 7/2001 | Knudsen et al. |
| 6,344,180 | B1 | 2/2002 | Holst et al. |
| 6,395,767 | B2 | 5/2002 | Robl et al. |
| 6,444,788 | B1 | 9/2002 | Staby |
| 6,458,924 | B2 | 10/2002 | Knudsen et al. |
| 6,468,798 | B1 | 10/2002 | Debs et al. |
| 6,528,486 | B1 | 3/2003 | Larsen et al. |
| 6,573,287 | B2 | 6/2003 | Sulsky et al. |
| 6,841,535 | B2 | 1/2005 | Divita et al. |
| 7,141,547 | B2 | 11/2006 | Rosen et al. |
| 9,040,481 | B2 * | 5/2015 | Habener ............... A61K 38/08 514/11.7 |
| 2001/0011071 | A1 | 8/2001 | Knudsen et al. |
| 2001/0047084 | A1 | 11/2001 | Knudsen et al. |
| 2002/0006899 | A1 | 1/2002 | Pospisilik et al. |
| 2002/0019411 | A1 | 2/2002 | Robl et al. |
| 2002/0110560 | A1 | 8/2002 | Demuth et al. |
| 2002/0183367 | A1 | 12/2002 | Sulsky et al. |
| 2003/0004095 | A1 | 1/2003 | Reimer et al. |
| 2003/0073626 | A1 | 4/2003 | Hathaway et al. |
| 2003/0091507 | A1 | 5/2003 | Holst et al. |
| 2003/0176357 | A1 | 9/2003 | Pospisilik et al. |
| 2003/0199451 | A1 | 10/2003 | Mogensen et al. |
| 2003/0199672 | A1 | 10/2003 | Knudsen et al. |
| 2003/0220243 | A1 | 11/2003 | Glaesner et al. |
| 2003/0220274 | A1 | 11/2003 | Oh et al. |
| 2003/0225102 | A1 | 12/2003 | Sankaranarayanan |
| 2004/0266678 | A1 | 12/2004 | Beeley et al. |
| 2006/0014241 | A1 | 1/2006 | Glaesner et al. |
| 2006/0183682 | A1 | 8/2006 | Juul-Mortensen |
| 2008/0194483 | A1 | 8/2008 | Brownlee |
| 2008/0300173 | A1 | 12/2008 | Defrees |
| 2009/0030178 | A1 | 1/2009 | Chang |
| 2009/0136585 | A1 | 5/2009 | Labhasetwar et al. |
| 2009/0227519 | A1 | 9/2009 | Balasubramaniam |
| 2009/0292108 | A1 | 11/2009 | Chen |
| 2010/0184645 | A1 | 7/2010 | Verdine et al. |
| 2010/0286024 | A1 | 11/2010 | Kanda |
| 2013/0288961 | A1 | 10/2013 | Habener et al. |
| 2014/0212472 | A1 | 7/2014 | Habener et al. |

(Continued)

FOREIGN PATENT DOCUMENTS

| | | |
|---|---|---|
| EP | 0708179 A2 | 10/1995 |
| EP | 0699686 A2 | 3/1996 |
| EP | 1076066 | 2/2001 |

(Continued)

OTHER PUBLICATIONS

Abu-Hamdah et al., "Clinical review: The extrapancreatic effects of glucagon-like peptide-1 and related peptides," J. Clin. Endocrinol. Metab., 94:1843-1852, Jun. 2009.

Authier et al., "Endosomal Proteolysis of Glucagon at Neutral pH Generates the Bioactive Degradation Product Miniglucagon-(19-29)," Endocrinology, 144(12):5353-5364, Dec. 2003.

Ban et al., "Cardioprotective and vasodilatory actions of glucagon-like peptide 1 receptor are mediated through both glucagon-like peptide 1 receptor-dependent and -independent pathways," Circulation, 117(18):2340-2350, Apr. 2008.

Ban et al., "Glucagon-like peptide (GLP)-1(9-36)amide- mediated cytoprotection is blocked by exendin (9-39) yet does not require the known GLP-1 receptor," Endocrinology, 151:1520-1531, February.

Bebernitz et al., "The Impact of Fatty Acid Oxidation on Energy Utilization: Targets and Therapy," Current Pharmaceutical Design, 8:1199-1227, Jun. 2002.

Bonny et al., "Cell-Permeable Peptide Inhibitors of JNK Novel Blockers of β-Cell Death," Diabetes, Jan. 2001, 50:77-82.

(Continued)

*Primary Examiner* — Marcela M Cordero Garcia
*Assistant Examiner* — Jia-Hai Lee
(74) *Attorney, Agent, or Firm* — Fish & Richardson P.C.

(57) ABSTRACT

Methods of treating obesity, metabolic syndrome, hepatic and non-hepatic steatosis, and diabetes using a pentapeptide, (Continued)

LVKGRamide, derived from the C-terminus of Glucagon-Like Peptide 1 (GLP-1).

13 Claims, 20 Drawing Sheets

Specification includes a Sequence Listing.

(56) References Cited

U.S. PATENT DOCUMENTS

2015/0133384 A1   5/2015   Habener et al.

FOREIGN PATENT DOCUMENTS

| EP | 1196444 | B1 | 6/2003 | | |
|---|---|---|---|---|---|
| EP | 1329458 | A2 | 7/2003 | | |
| EP | 0708179 | B1 | 12/2004 | | |
| WO | 1991/011457 | | 8/1991 | | |
| WO | 1996/006628 | | 3/1996 | | |
| WO | 1998/008871 | | 3/1998 | | |
| WO | 1998/039022 | | 9/1998 | | |
| WO | 1999/038501 | | 8/1999 | | |
| WO | 1999/043705 | | 9/1999 | | |
| WO | 1999/043706 | | 9/1999 | | |
| WO | 1999/043708 | | 9/1999 | | |
| WO | 1999/053064 | | 10/1999 | | |
| WO | 2000/077039 | | 12/2000 | | |
| WO | 2001/037850 | | 5/2001 | | |
| WO | 2001/068603 | | 9/2001 | | |
| WO | 2001/098331 | | 12/2001 | | |
| WO | 2002/047716 | | 6/2002 | | |
| WO | 2002/062764 | | 8/2002 | | |
| WO | 2002/083128 | | 10/2002 | | |
| WO | 2002/085406 | | 10/2002 | | |
| WO | 2003/018516 | | 3/2003 | | |
| WO | 2003/028626 | | 4/2003 | | |
| WO | 2003/038123 | | 5/2003 | | |
| WO | 2003/045977 | | 6/2003 | | |
| WO | 2003/061362 | | 7/2003 | | |
| WO | 2003/072195 | | 9/2003 | | |
| WO | 2003/099991 | | 12/2003 | | |
| WO | 2003/103572 | | 12/2003 | | |
| WO | 2005/060986 | | 7/2005 | | |
| WO | 2007/024899 | | 3/2007 | | |
| WO | 2007/030706 | | 3/2007 | | |
| WO | 2007/051987 | | 5/2007 | | |
| WO | 2007/061434 | | 5/2007 | | |
| WO | 2007/065156 | | 6/2007 | | |
| WO | 2009/051259 | | 4/2009 | | |
| WO | 2010/054326 | | 5/2010 | | |
| WO | WO2010054326 | A2 * | 5/2010 | ............ | C07K 7/04 |
| WO | 2010/093802 | | 8/2010 | | |
| WO | 2012/061466 | | 5/2012 | | |

OTHER PUBLICATIONS

Brun et al., "Intracellular targeting of truncated secretory peptides in the mammalian heart and brain," FASEB J., 20:732-734, Jan. 2006.
Carlson et al., "Regulation of the C/EBP-related gene gadd153 by glucose deprivation," Mol. Cell Biol., Aug. 1993, 13(8):4736-44.
Caron et al., "Intracellular Delivery of a Tat-eGFP Fusion Protein into Muscle Cells," Mol. Ther., Mar. 2001, 3(3):310-8.
Communication issued in EP 09825560.7 dated Apr. 15, 2014, 8 pages.
Dalle et al., "Miniglucagon (Glucagon 19-29) A Novel Regulator of the Pancreatic Islet Physiology," Diabetes, 51:406-412, Feb. 2002.
Dayhoff et al., "Establishing homologies in protein sequences," Methods Enzymol., 91:524-545, Jan. 1983.
De Meester et al., "CD26, let it cut or cut it down," Immunol. Today, 20:367-375, Aug. 1999.
Deacon, "Circulation and degradation of GIP and GLP-1," Horm. Metab. Res., 36:761-5, Nov. 2004.

Deacon, "Perspectives in Diabetes, Therapeutic Strategies Based on Glucagon-Like Peptide 1," Diabetes, Sep. 2004, 53:2181-2189.
Ding et al., "Exendin-4, a Glucagon-Like Protein-1 (GLP-1) Receptor Agonist, Reverses Hepatic Steatosis in ob/ob Mice," Hepatology, 43:173-181, Jan. 2006.
Dobrzyn et al., "Stearoyl-CoA desaturase 1 deficiency increases fatty acid oxidation by activating AMP-activated protein kinase in liver," Proc. Natl. Acad. Sci. USA, 101(17):6409-6414, Apr. 2004.
Drucker, "The biology of incretin hormones," Cell. Metab., 3:153-165, Mar. 2006.
Egan et al., "Glucagon-Like Peptide-1 Augments Insulin-Mediated Glucose Uptake in the Obese State," The Journal of Clinical Endocrinology & Metabolism, 87(8)3768-3773, Aug. 2002.
Elahi et al., "GLP-1 (9-36) amide, cleavage product of GLP-1 (7-36) amide, is a glucoregulatory peptide," Obesity (Silver Spring), 16(7):1501-1509, Jul. 2008.
Elahi et al., "The Insulinomimetic Actions of GLP-1(9-36) Amide, Cleavage Product of GLP-1(7-36) Amide," Diabetes, 55(Suppl 1):A85 (Abstract 363-OR), 2006.
European Office Action issued in EP09825560.7 dated Feb. 29, 2012 (8 pages).
European Office Action issued in EP09825560.7 dated Apr. 15, 2014 (8 pages).
European Office Action issued in EP09825560.7 dated Oct. 8, 2015 (6 pages).
European Office Action issued in EP12807290.7 dated Jun. 14, 2016 (7 pages).
European Search Report issued in EP09825560.7 dated Feb. 15, 2012 (8 pages).
European Search Report issued in EP12807290 dated Dec. 19, 2014 (10 pages).
Farooqui et al., "Metabolic syndrome as a risk factor for neurological disorders," Cell. Mol. Life. Sci., 69:741-762, Oct. 2011.
Ferrand et al., "Involvement of JAK2 upstream of the PI 3-kinase in cell-cell adhesion regulation by gastrin," Exp. Cell. Res., 301:128-138, Dec. 2004.
Flock et al., "Incretin receptors for glucagon-like peptide 1 and glucose-dependent insulinotropic polypeptide are essential for the sustained metabolic actions of vildagliptin in mice," Diabetes, 56:3006-13, Dec. 2007.
Fodor et al., "Recommendations for the management and treatment of dyslipidemia," Can. Med. Assoc. J., 2000, 162:1441-7.
Furuse et al., "Effects of various N-terminal fragments of glucagon-like peptide-1 (7-36) on food intake in the neonatal chick," Brain Research, 1998, 807:214-217.
Grattagliano et al., "Oxidative stress-induced risk factors associated with the metabolic syndrome: a unifying hypothesis," J. Nutr. Biochem., 19:491-504, Aug. 2008.
Green et al., "Degradation, receptor binding, insulin secreting and antihyperglycaemic actions of palmitate-derivatised native and A1a8-substituted GLP-1 analogues" Biol. Chem., Feb. 2004, 385:169-177.
Green et al., "GLP-1 and related peptides cause concentration-dependent relaxation of rat aorta through a pathway invoking KATP and CAMP," Arch. Biochem. Biophys., 478:136-142, Aug. 2008.
Haas et al., "Dissecting the Role of Insulin Resistance in the Metabolic Syndrome," Curr. Opin. Lipidol., 20:206-210, Jun. 2009.
Hansen et al., "Glucagon-like peptide-1-(7-36)amide is transformed to glucagon-like peptide-1-(9-36)amide by dipeptidyl peptidase IV in the capillaries supplying the L cells of the porcine intestine," Endocrinology, 140:5356-63, Nov. 1999.
Hashimoto et al., "A new inhibitor of mitochondrial fatty acid oxidation," J. Biochem., 119(6):1196-1201, Jun. 1996.
Hirst, "Towards the molecular mechanism of respiratory complex I," J. Biochem., 425:327-339, Dec. 2009.
Hupe-Sodmann et al., "Characterisation of the processing by human neutral endopeptidase 24.11 of GLP-1(7-36) amide and comparison of the substrate specificity of the enzyme for other glucagon-like peptides," Regul. Pept., 58(3):149-156, Aug. 1995.
Ibdah et al., "Lack of mitochondrial trifunctional protein in mice causes neonatal hypoglycemia and sudden death," J. Clin. Invest, 107:1403-1409, 2001.

(56) References Cited

OTHER PUBLICATIONS

Ibdah et al., "Mice Heterozygous for a Defect in Mitochondrial Trifunctional Protein Develop Hepatic Steatosis and Insulin Resistance," Gastroenterology, 128:1381-1390, May 2005.
International Preliminary Report on Patentability in International Application No. PCT/US2009/063746, dated May 19, 2011, 8 pages.
International Preliminary Report on Patentability in International Application No. PCT/US2011/058907, dated May 7, 2013, 5 pages.
International Preliminary Report on Patentability in International Application No. PCT/US2012/045537, dated Jan. 16, 2014, 8 pages.
International Search Report and Written Opinion in International Application No. PCT/US2012/045537, dated Jan. 29, 2013, 16 pages.
International Search Report in International Application No. PCT/US2011/058907, dated May 25, 2012, 3 pages.
International Search Report in International Application No. PCT/US2009/063746 dated Jun. 29, 2010, 15 pages.
Kieffer and Habener, "The glucagon-like peptides," Endocr. Rev., 20:876-913, Dec. 1999.
Knudsen et al., "Glucagon-like peptide-1-(9-36) amide is a major metabolite of glucagon-like peptide-1-(7-36) amide after in vivo administration of dogs, and it acts as an antagonist on the pancreatic receptor," European Journal of Pharmacology, 318:429-435, Dec. 1996.
Knudsen et al., "Potent derivatives of glucagon-like peptide-1 with pharmacokinetic properties suitable for once daily administration," J. Med. Chem., 43:1664-1669, May 2000.
Koonen et al., "Increased hepatic CD36 expression contributes to dyslipidemia associated with diet-induced obesity," Diabetes, 56:2863-2871, Dec. 2007.
Lambeir et al., "Dipeptidyl-peptidase IV from bench to bedside: an update on structural properties, functions, and clinical aspects of the enzyme DPP IV," Crit. Rev. Clin. Lab. Sci., 40:209-294, Jun. 2003.
Larter et al., "MCD-induced steatohepatitis is associated with hepatic adiponectin resistance and adipogenic transformation of hepatocytes," J Hepatol., 49:407-416, Sep. 2008.
Lee et al., "Efficient intracellular delivery of functional proteins using cationic polymer core/shell nanoparticles," Biomaterials, 2008, 29(9):1224-1232.
Li et al., "GLP-1 C-terminal structures affect its blood glucose lowering function," Journal of Peptide Science, 14:777-785, Jul. 2008.
Liu et al., "Prolonged treatment of primary hepatocytes with oleate induces insulin resistance through p38 mitogen-activated protein kinase," J. Biol. Chem., 282:14205-44212, May 2007.
Lovshin and Drucker, "Incretin-based therapies for type 2 diabetes mellitus," Nat. Rev. Endocrinol., 5:262-9, May 2009.
Luchsinger, "Diabetes, related conditions, and dementia," J Neurol Sci., 299:35-38, Dec. 2010.
Mayo et al., "Design of a Partial Peptide Mimetic of Anginex with Antiangiogenic and Anticancer Activity," J. Biol. Chem., Aug. 2003, 278:45746.
Meier et al., "The glucogon-like peptide-1 metabolite GLP-I(9-36)amide reduces postprandial glycemia independently of gastric emptying and insulin secretion in humans," Am. J. Physiol. Endocrinol. Metab., 290:E1118-E1123, Jun. 2006.
Meneilly et al., "Effects of 3 Months of Continuous Subcutaneous Administration of Glucagon-Like Peptide 1 in Elderly Patients with Type 2 Diabetes," Diabetes Care, 26(10):2835-2841, Oct. 2003.
Mojsov, "Structural requirements for biological activity of glucagon-like peptide-I," Int. J. Peptide Protein Res., 1992, 40:333-343.
Mu et al., "Chronic Inhibition of Dipeptidyl Peptidase-4 With a Sitagliptin Analog Preserves Pancreatic B-Cell Mass and Function in a Rodent Model of Type 2 Diabetes," Diabetes, Jun. 2006, 55:1695-1704.
Murphy et al., "Gastrin and gastrin receptor antagonists bind to both N- and C-terminal halves of the 78 kDa gastrin-binding protein," Int. J. Biochem. Cell. Biol., 28:1233-1240, Nov. 1996.

Nikolaidis et al., "Active metabolite of GLP-1 mediates myocardial glucose uptake and improves left ventricular performance in conscious dogs with dilated cardiomyopathy," Am. J. Physiol. Heart Circ. Physiol., 289:H2401-2408, Dec. 2005.
Oltman et al., "Role of the effect of inhibition of neutral endopeptidase on vascular and neural complications in streptozotocin-induced diabetic rats," Eur. J. Pharmacol., Jan. 2011, 650(2-3):556-562.
Ott et al., "Mitochondria, oxidative stress and cell death," Apoptosis, 12:913-922, May 2007.
Panza et al., "Metabolic Syndrome and Cognitive Impairment: Current Epidemiology and Possible Underlying Mechanisms," J. Alzheimers Dis., 21:691-724, Jun. 2010.
Parekh et al., "Reversal of diet-induced obesity and diabetes in C57BL/6J mice," Metabolism, 47:1089-1096, Sep. 1998.
Pathak et al., "Dipeptidyl Peptidase-4 (DPP-4) Inhibitors in the Management of Diabetes," Drug Class Review, Sep. 2010, 35(9):509-513.
Plamboeck et al., "Neutral endopeptidase 24.11 and dipeptidyl peptidase IV are both involved in regulating the metabolic stability of glucagon-like peptide-1 in vivo," Adv Exp Med Biol., 524:303-12, 2003.
Plamboeck et al., "Neutral endopeptidase 24.11 and dipeptidyl peptidase IV are both mediators of the degradation of glucagon-like peptide 1 in the anaesthetized pig," Diabetologia, 48(9):18824890, Jul. 2005.
Randle, "Regulatory interactions between lipids and carbohydrates: the glucose fatty acid cycle after 35 years," Diabetes Metab. Rev., 14:263-283, Dec. 1998.
Rodrigue-Way et al., "A growth hormone-releasing peptide promotes mitochondrial biogenesis and a fat burning-like phenotype through scavenger receptor CD36 in white adipocytes," Endocrinology, 148(3):1009-1018, Mar. 2007.
Roques et al., "Neutral endopeptidase 24.11: structure, inhibition, and experimental and clinical pharmacology," Pharmacol. Rev., 45:87-146, Mar. 1993.
Ryan et al., "Insulinotropic Hormone Glucagon-Like Peptide-1-(7-37) Appears Not to Augment Insulin-Mediated Glucose Uptake in Young Men during Euglycemia," Journal of Clinical Endocrinology and Metabolism, 83(7):2399-2404, 1998.
Sato et al., "Therapeutic peptides: technological advances driving peptides into development," Current Opinion in Biotechnology, 17(6):638-642, Dec. 2006.
She et al., "Adipogenic Transcriptional Regulation of Hepatic Stellate Cells," J, Biol, Chem,. 280:4959-4967, Feb. 2005.
Simonsen et al., "Inhibition of neutral endopeptidase 24.11 does not potentiate the improvement in glycemic control obtained with dipeptidyl peptidase-4 inhibition in diabetic Goto-Kakizaki rats," Horm. Metab. Res., 41:851-3, Nov. 2009.
Sonne et al., "Protective effects of GLP-1 analogues exendin-4 and GLP-1(9-36) amide against ischemia-reperfusion injury in rat heart," Regul. Pept., 146:243-249, Feb. 2008.
Standeven et al., "Neprilysin, obesity and the metabolic syndrome," Int J Obes (Lond), Nov. 1-10, 2010.
Stein et al., "Insulin sensitizers in nonalcoholic fatty liver disease and steatohepatitis," Current Status Advanced Ther., 26:893-907, Oct. 2009.
Supplementary European Search Report issued in EP09825560 dated Feb. 7, 2012, 7 pages.
Suzuki et al., "Comparison of the Effects of Various C-Terminal and N-Terminal Fragment Peptides of Glucagon-Like Peptide-1 on Insulin and Glucagon Release from the Isolated Perfused Rat Pancreas," Endocrinology, 1989, 125(6):3109-3114.
Szeto, "Cell-permeable, Mitochondrial-targeted, Peptide Antioxidants," AAPS Journal 2006; 8(2) Article 32, 7 pages.
Todd et al., "Glucagon-like peptide-1 (GLP-1): a trial of treatment in non-insulin-dependent diabetes mellitus," European Journal of Clinical Investigation, 27:533-536, Jun. 1997.
Tomas and Habener, "Insulin-like actions of glucagon-like peptide-1: A dual receptor hypothesis," Trends Endocrinol. Metab., 21:59-67, Feb. 2010.
Tomas et al., "Abstract 1915-P:GLP-1-Derived Pentapeptide GLP-1(32-36)amide Attenuates the Development of Obesity, Diabetes, Heaptic Steatosis and Increases Energy Expenditure in Diet-

(56) References Cited

OTHER PUBLICATIONS

Induced Obese Mice," 72nd Scientific Sessions, American Diabetes Association, (Jun. 2012) Retrieved from the Internet: URL:http://www.abstractsonline.com/Plan/AbstractPrintView.aspx?mID=2936&sKey=b266eaf6-c060-450a-9a54-ae244aae03af&cKey=e1f51b44-b39f-49dc-b2bd-44c011d595ea [retrieved on Dec. 18, 2014].

Tomas et al., "GLP-1(9-36)amide metabolite suppression of glucose production in isolated mouse hepatocytes," Horm. Metab. Res., 42:657-662, Aug. 2010.

Tomas et al., "GLP-1-derived nonapeptide GLP-1(28-36) amide inhibits weight gain and attenuates diabetes and hepatic steatosis in diet-induced obese mice," Regulatory Peptides, 169(1-3):43-48, May 2011.

Tomas et al., "GLP-1-derived nonapeptide GLP-1(28-36) amide targets to mitochondria and suppresses glucose production and oxidative stress in isolated mouse hepatocytes," Regulatory Peptides, 167(2-3):177-184, Jan. 2011.

Tomas et al., "Glucagon-like peptide-1(9-36)amide metabolite inhibits weight gain and attenuates diabetes and hepatic steatosis in diet-induced obese mice," Diabetes Obes Metab., 13:26-33, Jan. 2011.

Tsukamoto et al., "Fat paradox of steatohepatitis," J Gastroenterol Hepatol., 23 Suppl 1:S104-107, Mar. 2008.

Unger et al. "Lipid homeostasis, lipotoxicity and the metabolic syndrome," Biochimica et Biophysica Acta., 1801:209-214, Nov. 2010.

U.S. Final Office Action in U.S. Appl. No. 13/127,387, dated Jan. 14, 2014, 13 pages.

U.S. Final Office Action in U.S. Appl. No. 14/128,801, dated Jun. 29, 2015, 11 pages.

U.S. Final Office Action in U.S. Appl. No. 14/539,578, dated Mar. 17, 2016, 21 pages.

U.S. Non-Final Office Action in U.S. Appl. No. 13/127,387, dated Sep. 19, 2013, 17 pages.

U.S. Non-Final Office Action in U.S. Appl. No. 13/882,825, dated May 28, 2014, 34 pages.

U.S. Non-Final Office Action in U.S. Appl. No. 14/539,578, dated Sep. 21, 2015, 14 pages.

U.S. Non-Final Office Action in U.S. Appl. No. 14/128,801, dated Jan. 5, 2015, 18 pages.

U.S. Non-Final Office Action in U.S. Appl. No. 14/128,801, dated Feb. 19, 2016, 13 pages.

U.S. Notice of Allowance in U.S. Appl. No. 13/127,387, dated Jul. 21, 2014, 14 pages.

U.S. Notice of Allowance in U.S. Appl. No. 13/882,825, dated Jan. 30, 2015, 17 pages.

Vahl et al., "Effects of GLP-1-(7-36)NH2, GLP-1-(7-37), and GLP-1-(9-36)NH2 on Intravenous Glucose Tolerance and Glucose-Induced Insulin Secretion in Healthy Humans," The Journal of Clinical Endocrinology & Metabolism, Apr. 2003, 88(4):1772-1779.

Wanders et al., "Disorders of mitochondrial fatty acyl-CoA $\beta$-oxidation," J. Inher. Metab. Dis., 22:442-487, Jun. 1999.

Xiong et al., "New insight into the mechanisms underlying the function of the incretin hormone glucagon-like peptide-1 in pancreatic $\beta$-cells," Landes Bioscience, 2012, 4(6):359-365.

Zander et al., "Effect of 6-week course of glucagon-like peptide 1 on glycaemic control, insulin sensitivity, and betta-cell function in type 2 diabetes: a parallel-group study," The Lancet, 359:824-830, Mar. 2002.

Zhang et al., "Continuous stimulation of human glucagon-like peptide-1 (7-36) amide in a mouse model (NOD) delays onset of autoimmune type 1 diabetes," Diabetologia, 50:1900-1999, Jul. 2007.

Zhao et al., "Cell-permeable Peptide Antioxidants Targeted to Inner Mitochondrial Membrane inhibit Mitochondrial Swelling, Oxidative Cell Death, and Reperfusion Injury," J. Biol. Chem., 279:34682-90, Jul. 2004.

U.S. Non-Final Office Action in U.S. Appl. No. 14/539,578, dated Jan. 11, 2017, 17 pages.

European Office Action in Application No. 12807290.7, dated Jun. 16, 2017, 6 pages.

\* cited by examiner

|  | LFD | VHFD | |
|---|---|---|---|
|  |  | Vehicle | GLP-1(32-36)a |
| Plasma Glycerol | 0.128± 0.02 | 0.25± 0.04 | 0.128± 0.025* |
| Plasma Triglyceride | 0.58± 0.06 | 0.65± 0.06 | 0.33± 0.020** |

LFD                    0.13 +/- 0.02        0.58 +/- 0.06

FIG. 6C ns of the pentapeptide GLP-13(2-36)amide or control
METHODS OF TREATMENT USING A PENTAPEPTIDE DERIVED FROM THE C-TERMINUS OF GLUCAGON-LIKE PEPTIDE 1 (GLP-1)

CLAIM OF PRIORITY

This application is a continuation of U.S. patent application Ser. No. 14/128,801, with a 371 filing date of Mar. 21, 2014, which is a U.S. National Phase Application under 35 U.S.C. § 371 of International Patent Application No. PCT/US2012/045537, filed on Jul. 5, 2012, which claims the benefit of U.S. Provisional Patent Application Ser. No. 61/504,866, filed Jul. 6, 2011, and Ser. No. 61/546,698, filed on Oct. 13, 2011, the entire contents of the foregoing are hereby incorporated by reference.

TECHNICAL FIELD

This invention relates to methods of treating obesity, metabolic syndrome, hepatic and non-hepatic steatosis, and diabetes using a pentapeptide, LVKGRamide, derived from the C-terminus of Glucagon-Like Peptide 1 (GLP-1).

BACKGROUND

The prevalence of obesity-related metabolic syndrome consisting of diabetes, hypertension, hypertriglyceridemia, hepatic steatosis, and accelerated atherosclerosis is increasing worldwide. No satisfactory treatments are available for obesity and the metabolic syndrome.

SUMMARY

At least in part, the present invention is based on the discovery that a pentapeptide, GLP-1(32-36)amide (LVKGRamide (SEQ ID NO:1)) derived from the C-terminus of the glucoincretin hormone GLP-1 curtails the development of obesity, insulin resistance, diabetes, hypertriglyceridemia, and hepatic steatosis, and increases energy expenditure.

Thus, in a first aspect, the invention provides isolated peptides consisting essentially of a sequence Leu-Val-(Lys/Arg)-Gly-Arg-Xaa (SEQ ID NO:3), wherein Xaa can be Gly, Gly-Arg, Gly-Arg-Gly, or absent.

In some embodiments, the peptide is amidated. The lysine (K) and arginine (R) in LVKGRamide are in a configuration potentially acceptable for acetylation. Amidation occurs at the C-terminal amino acid of some peptides. In some embodiments, when the C terminus is an Arg, the arginine is amidated. In some embodiments, e.g., the corresponding hexapeptide, LVKGRG, the G, glycine, is not amidated. In some embodiments, one or more amino acids are modified by attachment of a fatty acid, e.g., palmitate or oleate.

In a further aspect, the invention provides fusion peptides comprising a first portion consisting essentially of a sequence: Leu-Val-(Lys/Arg)-Gly-Arg-Xaa (SEQ ID NO:3), wherein Xaa can be Gly, Gly-Arg, Gly-Arg-Gly, or absent, fused to a cell-penetrating peptide. In some embodiments, the cell-penetrating peptide is fused on the C-terminus of the peptide. In some embodiments, the cell-penetrating peptide is fused on the N-terminus of the peptide. In some embodiments, the cell-penetrating peptide is selected from the group consisting of HIV-derived TAT peptide, penetratins, transportans, SS peptides, and hCT derived cell-penetrating peptides.

In yet another aspect, the invention provides isolated nucleic acids encoding the peptides or fusion peptides described herein, and host cells including and/or expressing the isolated nucleic acids.

In an additional aspect, the invention provides therapeutic compositions including the peptides or described herein in a physiologically acceptable carrier. In some embodiments, the compositions further include at least one cell-penetrating agent, e.g., a cationic liposome.

Also provided herein is the use of the peptides or fusion peptides described herein in the treatment of obesity or an obesity-related disorder. In some embodiments, the obesity-related disorder is diabetes or the metabolic syndrome, hepatic steatosis, non-hepatic steatosis or hypertriglyceridemia.

In yet another aspect, the invention features methods for treating obesity or an obesity-related disorder in a subject. The methods include administering a therapeutically effective amount of a peptide or fusion peptide as described herein. In some embodiments, the obesity-related disorder is diabetes or the metabolic syndrome, hepatic steatosis, non-hepatic steatosis or hypertriglyceridemia.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 5A: Fasting plasma glucose levels *p<0.0004 vehicle vs. GLP-1(32-36)a. FIG. 5B: Fasting insulin levels *p<0.042 vehicle vs. GLP-1(32-36)a. The studies are in mice fed a VHFD for 15 weeks, two weeks before beginning the continuous infusions of either control vehicle or pentapeptide. Continuous infusions of vehicle or pentapeptide GLP-1(32-36)amide were give during weeks 17 to 29 of diet (23 to 35 weeks of age). Weeks denoted on the ordinate scales refers to weeks of age. N=6 mice per group. Values are means+/−SEMs.

FIG. 6C is a table showing continuous infusion of GLP-1(32-36)amide for 16-weeks improves plasma circulating levels of glycerol and triglyceride in mice fed on a 60% fat diet (VHFD) for 24-weeks. *p<0.02, peptide vs. vehicle; **p<0.008 peptide vs. vehicle.

DETAILED DESCRIPTION

Figure 1A:
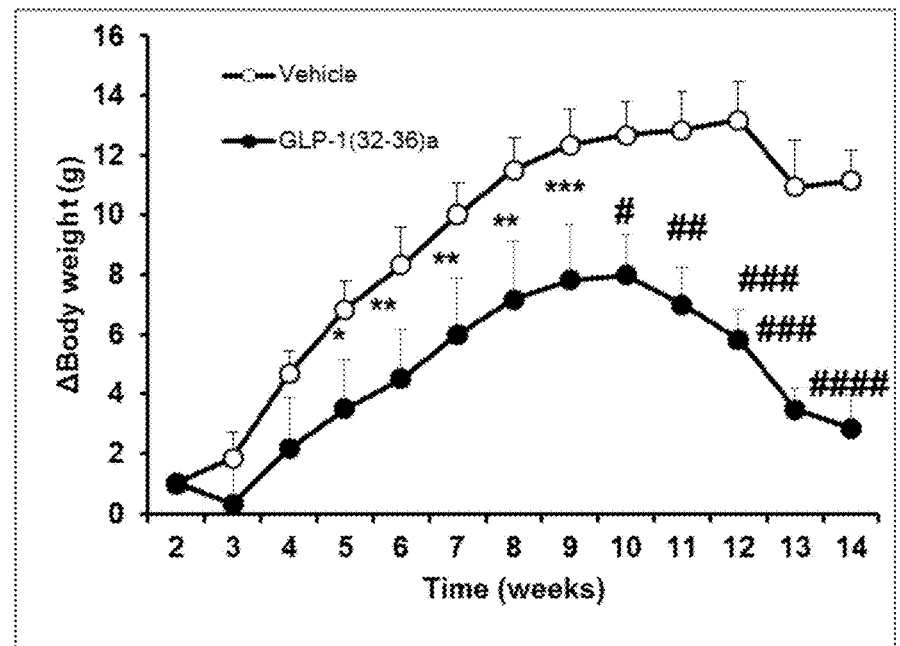
FIGS. 1A-B show that GLP-1-derived pentapeptide, GLP-1(32-36)amide (LVKGRamide) (SEQ ID NO:1) curtailment of weight gain in diet-induced obese mice. The data encompass twelve weeks, from week 2 to week 14 of continuous infusions of control vehicle and GLP-1(32-36) amide. GLP-1(32-36)amide was administered to mice via mini-osmopumps (Alzet #1004) at a rate of 40 nanomoles/Kg body weight/24 hours. Male C57bl/6j mice were placed on a high fat diet (Research Diets, #D12492, 60 kcal % fat) at six weeks of age and continued for 17 weeks before starting osmopump infusions at age 23 weeks. 1A. Line graph showing time-dependent changes in body weight (BW) over fourteen weeks of infusions of control vehicle and pentapeptide GLP-1(32-36)amide. (*) $p<0.05$ versus vehicle control; () $p<0.04$ versus vehicle control; (*) $p<0.034$; (#) $p<0.01$; (##) $p<0.004$; (###) $p<0.0006, 0.0007$; (####) $p<0.0001$. 1B. Bar graph showing average weekly weight changes over ten weeks of infusions (weeks 2 to 14) shown in FIG. 1A. N=six mice per group. Values are means+/−SEMs. *$p<0.013$ peptide vs. vehicle. At week two of infusions of vehicle and pentapeptide the mice weighed 37.2 and 38.2 gms (averages of six mice), respectively. N=six mice per group.

Obesity-related metabolic syndrome is manifested as diabetes, hypertension, hyper-lipidemia, hepatic steatosis, and accelerated atherosclerosis. The pathophysiology underlying the metabolic syndrome is the development of insulin resistance and resulting increased oxidative stress [1,2]. Currently, effective treatments for obesity and metabolic syndrome are not available. As described herein, a GLP-1 (32-36)amide pentapeptide (LVKGRamide) (SEQ ID NO:1) derived from the C-terminus of the glucoincretin hormone glucagon-like peptide-1 (GLP-1) curtails weight gain and the development of the metabolic syndrome in an animal model of diet-induced obesity.

GLP-1 is a glucoincretin hormone that augments glucose-dependent insulin secretion. GLP-1 receptor agonists are in use for the treatment of type 2 diabetes based on their stimulation of insulin secretion and a lowering of plasma glucose and HgbA1C levels [3,4]. It is generally believed that the full-length receptor agonist forms of GLP-1, such as GLP-1(7-36)amide, are rapidly inactivated in the circulation via cleavages by the endopeptidases diaminopeptidyl peptidase-4 and by neprilysin, a neutral endopepdidase (NEP 24.11) known as neprilysin [5,6]. The removal of the first two amino acids of GLP-1(7-36)amide gives rise to GLP-1(9-36) amide devoid of insulin-releasing activities and NEP 24.11 cleaves GLP-1 into several small peptides [7]. However, it was postulated earlier that cleavages of GLP-1 by the endopeptidases Dpp4 and neprilysin do not degrade the peptide but rather generate new C-terminal peptides with insulin-like actions on insulin-responsive target tissues [8]. Recent evidence indicates that GLP-1(9-36)amide, the product of cleavage of GLP-1 by Dpp4, exerts insulin-like and anti-oxidant cytoprotective actions on heart, vasculature, and liver [9-16]. Infusions of GLP-1(9-36)amide in obese, insulin-resistant human subjects suppresses hepatic glucose production without effect on plasma insulin levels [14]. Continuous infusion of GLP-1(9-36)amide for eight weeks in diet-induced mice curtails weight gain, increases energy expenditure, and inhibits the development of insulin resistance, diabetes and hepatic steatosis [16]. Furthermore, Infusions of the nonapeptide, GLP-1(28-36)amide, a product of the cleavage of GLP-1 by neprilysin [7], in diet-induced mice inhibits weight gain, the development of diabetes, hepatic steatosis, and increases energy expenditure [17]. The nonapeptide was found to enter isolated insulin-resistant mouse hepatocytes in vitro, target to mitochondria, and to suppress glucose production, reactive oxygen species, and to increase cellular ATP levels [18]. Notably, the actions of the GLP-1-derived C-terminal peptides, GLP-1(9-36) amide and GLP-1(28-36)amide appear to occur selectively in obese, insulin-resistant conditions and not in lean, insulin-sensitive human subjects [14] or mice [17] and occur by mechanisms independent of the GLP-1 receptor. Therefore, much new evidence indicates that GLP-1-derived peptides exert extrapancreatic actions on insulin-resistant tissues independent of the GLP-1 receptor [8,19].

GLP-1 C-Terminal Peptides, Fusion Peptides, Peptidomimetics, and Modifications

The GLP-1 C-terminal peptides described herein include the sequence LVKGRamide (SEQ ID NO:1), or a variant thereof. Variants include peptides in which the sequence is C-terminally extended, e.g., LVKGRG (SEQ ID NO:4), or LVRGRG (SEQ ID NO:5), or in which one or more amino acids are conservatively substituted, for example LVRGRamide (SEQ ID NO: 6), in which Lysine 34 (the numbering refers to the full-length GLP-1) is changed to Arginine. In some embodiments the peptides also include the sequence FIAW on the N-terminus. Methods for making these peptides are known in the art, e.g., using chemical synthesis or expression in a host cell.

Fusion Peptides

In some embodiments, the peptides also include a cell-penetrating moiety that facilitates delivery of the peptides to the intracellular space, e.g., HIV-derived TAT peptide, penetratins, transportans, SS peptides (alternating aromatic residues and basic amino acids (aromatic-cationic peptides)), SA, SM, or SNL peptides, or hCT derived cell-penetrating peptides, see, e.g., Caron et al., (2001) Mol Ther. 3(3):310-8; Langel, *Cell-Penetrating Peptides: Processes and Applications* (CRC Press, Boca Raton Fla. 2002); El-Andaloussi et al., (2005) Curr Pharm Des. 11(28):3597-611; Lindgren et al., Trends Pharmacol Sci. 21(3):99-103 (2000); Zhao et al., J Biol Chem 279:34682-34690 (2004); Szeto, AAPS Journal 2006; 8 (2) Article 32; Deshayes et al., (2005) Cell Mol Life Sci. 62(16):1839-49; Horn et al., J Med. Chem., 46:1799 (2003); Bonny et al., Diabetes, 50:77-82 (2001), and U.S. Pat. Nos. 6,841,535 and 7,576,058 and references cited therein. In some embodiments the cell-penetrating moiety is linked to the peptide, e.g., as a single fusion protein; thus, the invention includes fusion proteins comprising a GLP-1 C-terminal peptide as described herein and a cell-penetrating peptide, e.g., TAT, penetratins, transportans, or hCT derived cell-penetrating peptides. In some embodiments, the cell-penetrating peptide is attached to the N-terminus of the GLP-1 C-terminal peptide; in some embodiments, the cell-penetrating peptide is attached to the C-terminus of the GLP-1 C-terminal peptide. In some embodiments, the fusion protein further comprises a cleavable moiety as known in the art between the cell-penetrating peptide and the GLP-1 C-terminal peptide that cleaves off the cell-penetrating peptide, leaving the GLP-1 C-terminal peptide intact.

Peptidomimetics

In some embodiments, the peptides disclosed herein can be modified according to the methods known in the art for producing peptidomimetics. See, e.g., Kazmierski, W. M., ed., Peptidomimetics Protocols, Human Press (Totowa N.J. 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N terminus to the C terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include beta-amino acids, beta-substituted beta-amino acids ("beta3-amino acids"), phosphorous analogs of amino acids, such as a-amino phosphonic acids and b-amino phosphinic acids, and amino acids having non-peptide linkages. Artificial amino acids can be used to create peptidomimetics, such as peptoid oligomers (e.g., peptoid amide or ester analogues), beta-peptides, cyclic peptides, oligourea or oligocarbamate peptides; or heterocyclic ring molecules. Exemplary retro-inverso peptidomimetics include RGKVL (SEQ ID NO: 8), GRGKVL (SEQ ID NO: 9), or RGRGKVL (SEQ ID NO: 10), wherein the sequences include all D-amino acids.

Modifications

The peptide sequences described herein can be modified, e.g., by modification of one or more amino acid residues of a peptide by chemical means, either with or without an enzyme, e.g., by alkylation, acylation, ester formation, amide formation, e.g., at the carboxy terminus, or biotinylation, e.g., of the amino terminus. In some embodiments, the peptides are modified by the addition of a lipophilic substituent (e.g., a fatty acid) to an amino acid, e.g., to the Lysine. In some embodiments, the peptides include one or more of an N-terminal imidazole group, or a C-terminal amide group. In some embodiments, the epsilon-amino group of Lys34 is substituted with a lipophilic substituent, e.g., of about 4-40 carbon atoms, e.g., 8-25 carbon atoms. Examples include branched and unbranched C6-C20 acyl groups. Exemplary lipophilic substituents, and methods of attaching the same (including via an optional linker) are provided in U.S. Pat. No. 6,268,343 and Knudsen et al., J. Med. Chem. 43:1664-1669 (2000). In some embodiments, the lipophilic substituent is a fatty acid selected from the group consisting of straight-chain or branched fatty acids, e.g., oleic acid, caprylic acid, palmitic acid, and salts thereof.

In some embodiments, the peptide sequences are modified by substituting one or more amino acid residues of the parent peptide with another amino acid residue. In some embodiments, the total number of different amino acids between the sequence-modified peptide and the corresponding native form of the GLP-1 C-terminal peptide is up to five, e.g., up to four amino acid residues, up to three amino acid residues, up to two amino acid residues, or one amino acid residue.

In some embodiments, the total number of different amino acids does not exceed four. In some embodiments, the number of different amino acids is three, two, or one. In order to determine the number of different amino acids, one should compare the amino acid sequence of the sequence-modified GLP-1 peptide derivative with the corresponding native GLP-1 C-terminal fragment.

A number of suitable GLP-1 sequence analogues and modifications are described in the art, see, e.g., EP 0708179; WO 91/11457; U.S. Pat. No. 6,268,343).

Nucleic Acids, Vectors, and Host Cells

In one aspect, the invention includes nucleic acids encoding a GLP-1 C terminal peptide or modified peptide as described herein. For example, the invention includes nucleic acids encoding peptides that include a sequence set forth herein, e.g., the sequence SEQ ID NO:1 or 2. Nucleic acids disclosed herein also include nucleic acids encoding certain modified GLP-1 C-terminal pentapeptides, e.g., retro-GLP-1 C-terminal pentapeptides, GLP-1 C-terminal pentapeptides linked to a cellular internalization (carrier) sequence, and retro-GLP-1 C-terminal pentapeptides linked to a carrier sequence.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Also included in the invention are genetic constructs (e.g., vectors and plasmids) that include a nucleic acid encoding a peptide described herein operably linked to a transcription and/or translation sequence that enables expression of the peptide, e.g., expression vectors. A selected nucleic acid, e.g., a DNA molecule encoding a peptide described herein, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain a nucleic acid disclosed herein. A transformed cell is a cell into which (or into an ancestor of which) has been introduced, by means of recombinant DNA techniques, a nucleic acid encoding a peptide described herein that binds HSP-90 and/or induces apoptosis in a tumor cell. Both prokaryotic and eukaryotic cells, e.g., mammalian cells (e.g., tumor cell), yeast, fungi, and bacteria (such as *Escherichia coli*), can be host cells. An engineered cell exemplary of the type included in the invention is a tumor cell that expresses a GLP-1 C-terminal peptide.

Methods of Treatment

The methods described herein include methods for the treatment of obesity and disorders associated with obesity, e.g., diabetes and metabolic syndrome; steatotic disease, e.g., hepatic steatosis; and hypertriglyceridemia. In some embodiments, the disorder is diet-induced obesity, e.g., high-calorie or high-fat diet induced obesity. Generally, the methods include administering a therapeutically effective amount of a GLP-1 C-terminal peptide or peptidomimetic as described herein, to a subject who is in need of, or who has been determined to be in need of, such treatment.

As used in this context, to "treat" means to ameliorate at least one symptom of obesity or a disorder associated with obesity. Often, obesity results in hyperglycemia; thus, a treatment can result in a reduction in blood glucose levels and a return or approach to normoglycemia. Administration of a therapeutically effective amount of a compound described herein for the treatment of obesity will result in decreased body weight or fat.

Administration of a therapeutically effective amount of a compound described herein for the treatment of fatty liver disease (FLD) will result in, e.g., a decrease or stabilization of fat levels in the liver; a decrease or stabilization of inflammation levels in the liver; or a reduction, delay or prevention of development of NASH, fibrosis, cirrhosis, or liver failure. In some embodiments, administration of a therapeutically effective amount of a compound described herein for the treatment of FLD will result in decreased or no increase in intra-cytoplasmic accumulation of triglyceride (neutral fats), and an improvement or no decline in liver function.

Diabetic and Pre-Diabetic Subjects

In some embodiments, the subjects treated by the methods described herein have diabetes, i.e., are diabetic. A person who is diabetic has one or more of a Fasting Plasma Glucose Test result of 126 mg/dL or more; a 2-Hour Plasma Glucose Result in an Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and beta-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes. Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in Table 2.

TABLE 2

| Category | BMI |
|---|---|
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Metabolic Syndrome

In some embodiments, the methods include determining whether a subject has the metabolic syndrome, and selecting the subject if they do have the metabolic syndrome, then administering an inhibitory nucleic acid as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes. 37(12):1595-1607 (1988)), refers to a clustering of obesity, dyslipidemia, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Fatty Liver Disease (FLD)

Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardiovascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma. FLD can be caused by excessive alcohol consumption (alcoholic hepatitis), drugs (such as valproic acid and corticosteroids (e.g., cortisone or prednisone)), excessive Vitamin A, and obesity. A diagnosis of NAFLD or NASH can be made by methods known in the art, e.g., by histological examination of liver biopsy samples.

In some embodiments, the methods include determining whether a subject has FLD, and selecting the subject if they do have FLD, then administering a dose of a GLP-1 C-terminal peptide or peptidomimetic as described herein. Determining whether a subject has FLD can include reviewing their medical history, or ordering or performing such tests as are necessary to establish a diagnosis.

Most individuals with FLD are asymptomatic; the condition is usually discovered incidentally as a result of abnormal liver function tests or hepatomegaly, e.g., noted in an unrelated medical condition. Elevated liver biochemistry is found in 50% of patients with simple steatosis (see, e.g., Sleisenger, *Sleisenger and Fordtran's Gastrointestinal and Liver Disease*. Philadelphia: W.B. Saunders Company (2006)). In general, the diagnosis begins with the presence of elevations in liver tests that are included in routine blood test panels, such as alanine aminotransferase (ALT) or aspartate aminotransferase (AST). Even modest, subclinical increases in hepatic fat accumulation have been shown to be an early component in the progressive pathogenesis of metabolic syndrome (see, e.g., Almeda-Valdes et al., Ann. Hepatol. 8 Suppl 1:S18-24 (2009); Polyzos et al., Curr Mol Med. 9(3):299-314 (2009); Byrne et al., Clin. Sci. (Lond). 116(7):539-64 (2009)).

Imaging studies are often obtained during evaluation process. Ultrasonography reveals a "bright" liver with increased echogenicity. Thus, medical imaging can aid in diagnosis of fatty liver; fatty livers have lower density than spleen on computed tomography (CT) and fat appears bright in T1-weighted magnetic resonance images (Mills). Making a differential diagnosis of Nonalcoholic Steatohepatitis (NASH), as opposed to simple fatty liver, is done using a liver biopsy. For a liver biopsy, a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or Nonalcoholic Fatty Liver Disease (NAFLD) is diagnosed. Thus, histological diagnosis by liver biopsy is sought when assessment of severity is indicated.

Non-Hepatic Steatosis

Although the liver is most often associated with steatosis, it can occur in any organ, including but not limited to kidneys (renal steatosis, see, e.g., Bobulescu et al., Am J Physiol Renal Physiol. 2008 June; 294(6):F1315-22), heart (cardiac steatosis, see, e.g., McGavock et al., Circulation. 2007 Sep. 4; 116(10):1170-5; McGavock et al., Ann Intern Med. 2006 Apr. 4; 144(7):517-24), skeletal muscle, and vasculature (e.g., atherosclerosis); thus, the present methods may also be used to treat those conditions. See, e.g., Federico et al., World J Gastroenterol. 2010 Oct. 14; 16(38): 4762-72.

Hypertriglyceridemia

Hypertriglyceridemia, or high blood levels of triglycerides, has been associated with atherosclerosis, even in the absence of hypercholesterolemia. Severe hypertriglyceridemia (e.g., levels greater than 1000 mg/dL) is also a precursor to pancreatitis. Caused or exacerbated by uncontrolled diabetes mellitus, obesity, and sedentary habits, hypertriglyceridemia is a risk factor for coronary artery disease (CAD). Hypertriglyceridemia is typically diagnosed in the presence of a fasting plasma triglyceride measurement that is increased, typically above the $90^{th}$ or $95^{th}$ percentile for age and sex. The Adult Treatment Panel III of the National Cholesterol Education Program (JAMA 2001; 285: 2486-97) has suggested 4 triglyceride strata in the context of assessment of risk of cardiovascular disease: normal (<1.7 mmol/L), borderline high (1.7-2.3 mmol/L), high (2.3-5.6 mmol/L) and very high (>5.6 mmol/L). See, e.g., Yuan et al., CMAJ, 176 (8):1113-1120 (2007); Durrington, Lancet 362: 717 (2003); Ford et al., Arch Intern Med 169:572 (2009).

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include GLP-1 C-terminal peptides described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In some embodiments, the GLP-1 C-terminal peptides are formulated with a cell penetrating agent as known in the art, e.g., liposomes or micelles. Biodegradable microparticle or nanoparticle delivery systems that increase intracellular uptake, e.g., polymeric and surface modified nanoparticles as described in US 2009/0136585 and, can also be used. Examples include poly DL-lactide-co-glycolide (PLGA) nanoparticles, e.g., surface-modified with known surface-modifying agents, such as heparin, dodecylmethylammonium bromide (DMAB), DEAE-Dextran, lipofectin, and fibrinogen (see, e.g. Song et al., J. Control. Release, 54:201-211 (1998); Labhasetwar et al., J. Pharm. Sci., 87:1229-34 (1998); Lee et al., Biomaterials 29(9):1224-1232 (2008); and US 2009/0136585.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1

GLP-1-Derived Pentapeptide GLP-1(32-36)amide Increases Basal Energy Expenditure, Inhibits Weight Gain, the Development of Insulin Resistance, and Hepatic Steatosis in Diet-Induced Obese Mice Because the C-terminal pentapeptide, GLP-1(32-36) amide, LVKGRamide, was also shown to be a major end-product of the proteolysis of GLP-1 by neprilysin [7] in addition to the nonapeptide GLP-1(28-36)amide, FIAWLVKGRamide, the actions of the pentapeptide, LVKGRamide [8], were investigated in diet-induced obese mice that develop the metabolic syndrome and in isolated insulin-resistant mouse hepatocytes. Similar to the nonapeptide reported on earlier [17,18], the pentapeptide curtails weight gain, inhibits the development of insulin resistance, diabetes, hepatic steatosis, and increases basal energy expenditure in the diet-induced mouse model of metabolic syndrome and suppresses glucose production and ROS levels in isolated insulin-resistant mouse hepatocytes. These findings of novel insulin-like actions of GLP-1-derived C-terminal penta and nona peptides in obese mice and isolated hepatocytes suggest the possibility that they may prove to be useful treatments for obesity-related diabetes and the metabolic syndrome.

Materials and Methods

Reagents

GLP-1(32-36)amide, LVKGRamide, was prepared by solid phase peptide synthesis in the MGH Biopolymers Core Laboratory. The peptide was >98% valid peptide by HPLC and mass spectrometry analyses. Osmotic pumps (Alzet #1004 osmopumps) were from Alzet, Cupertino, Calif. Other reagents were from Sigma-Aldrich, St Louis, Mo.

Mice

Male C57bl/6 mice at 6 of age were placed on a very high-fat diet (VHFD, 60% fat, Research Diets) for 17 weeks. At week 17 the mice on the high-fat diet, corresponding to 23 weeks of age, mini-osmopumps containing either vehicle or GLP-1(32-36)amide were implanted subcutaneously for delivery of peptide or vehicle over 16 weeks. Forty nanomoles (20 micrograms) of GLP-1(32-36) was diluted in saline containing 0.1% human serum albumin and were infused at a rate of forty nanomoles/kgBW/day for 16 weeks to achieve an estimated concentration of approximately 100 pM similar to that reported by infusions of GLP-1(7-36) amide [20]. For infusions longer than 4 weeks additional osmopumps with peptide were implanted at the end of each 4 weeks infusion. Body weights were recorded weekly. Food consumption was assessed every 3 to 4 days by weight. Energy intake (kcal/gm BW/week) and Feed Efficiency Index (FEI) were evaluated during the infusions of vehicle or peptide. The latter provides a measure of the efficiency of caloric conversion to body weight and it is calculated by determining the grams of body weight gain per cage/Kcal of food consumed per cage, [21]. There was no observable change in the activities of the mice amongst the various experimental groups. Mouse care was conducted under approval by the MGH Institutional Animal Care Use Committee.

Metabolic Parameters Determined in a Closed Metabolic System

Mice were single-caged for three days acclimatization and then transferred to single-cage metabolic chambers in a PhenoMaster/LabMaster system (TSE-Systems, Inc., Chesterfield, Mo.) for measurements of oxygen consumption, $CO_2$, physical activity, and food intake during light and dark cycles for a period of 72 hrs.

Dual Energy X-Ray Absorptiometry (DXA)

Mice were anesthetized with 0.02 ml of a 2% tribromoethanol solution per gram of body weight and scanned with a dual X-ray apparatus (Lunar Piximus, GE Medical Systems, Wauwatosa, Wis.). Total, fat, and lean body mass was quantitatively determined.

Electron Spray and Liquid Chromatography Mass Spectrometry

Mice were given single i.v. injections of the propeptide, GLP-1(9-36)amide and blood samples were taken at times 2, 5, and 10 min. Plasma was assayed for the presence of GLP-1(9-36)amide, GLP-1(28-36)amide, and GLP-1(32-36)amide by electron spray mass spectrometry (ES-MS. Pooled plasma samples collected after a 28 day continuous infusion of GLP-1(9-36)amide or GLP-1(28-36)amide in mice were assayed for peptide concentrations by liquid chromatography mass spectrometry (LC-MS).

Plasma Glucose and Insulin Measurements

Plasma obtained by tail nick from mice fasted for 16 hrs was assayed for glucose by using the one touch ultra-mini glucometer (Life Scan, Johnson and Johnson company) and for insulin with a rat/mouse Elisa kit (Crystal Chem, Downers Grove, Ill.).

Analyses of Liver Samples for Lipid Accumulation and Triglyceride Content.

Representative samples (2-3 gms) of livers were obtained and quick frozen on solid CO2 at the time of sacrifice and necropsy. The samples were subsequently homogenized and triglycerides were extracted and measured using a colorimetric enzymatic assay (Serum Triglyceride Determination kit, Sigma).

Isolated Mouse Hepatocytes

C57bl/6J mice from 10-12 weeks of age were purchased from Jackson Laboratories, Bar Harbor, Me. Diet-induced obesity mice (DIO) were obtained after C57bl/6J mice of 10-12 weeks of age were fed a high-fat diet (60% kcal fat, D12492, Research Diets, New Brunswick, N.J.) for 9 weeks. Mice were fasted overnight (16 hrs) and primary hepatocytes were isolated from the livers using a collagen and perfusion gradient purification [15]. Cells were first seeded using a Dulbecco's modified Eagle's medium (DMEM) supplemented with 10% FBS, 1 g/L glucose, 2 mmol/l sodium pyruvate, 1 micromol/L dexamethasone, and 0.1 micromol/L insulin, and later maintained in DMEM with 0.2% BSA, 1 g/L glucose, 0.1 micromol/L dexamethasone, and 1 nmol/L insulin. Mice were housed and treated in accord with the regulations of the MGH Institutional Animal Care Utilization Committee.

Glucose Production Assay

Primary hepatocytes ($2 \times 10^5$ cells per well in twelve-well plates) were pre-treated with GLP-1(32-36)amide for 1 hour followed by the stimulation of insulin resistance by the addition of cAMP (10 microM)/dexamethasone (50 mM)/sodium lactate (2 mM) in glucose-free DMEM without phenol red. The culture media were collected for measuring glucose concentration with a colorimetric glucose assay kit (Sigma). The readings were then normalized to total protein content determined from whole-cell lysates.

Glucose Tolerance Test (ipGTT) and Fasting Insulin Test Protocol

Mice were maintained in a normal light/dark cycle according to the standard protocols of the MGH Animal Care and Use Committee. Mice were tested with age matched or litter mate controls and 6 mice per group are required. Mice were fasted for 16 hours: beginning around 6 pm the evening prior to the GTT mice are transferred to a new cage with water but no food and a DO NOT FEED card is placed in the cardholder. The following morning the mice were prepared for the glucose tolerance test: animals were weighed, the tail was nicked with a fresh razor blade by a horizontal cut of the very end, ~35 to 50 microliters of blood is massaged from the tail to an eppendorf tube which is immediately placed on ice, baseline blood glucose is measured by the glucose oxidase method using a Glucometer Elite glucometer, and 2 grams/kg body weight of 20% D-glucose is drawn up in a Beckton Dickenson D 29 gage ½" insulin syringe (one unit of D-glucose for every gram of body weight). Animals were then transferred to individually labeled 1000 cc cardboard soup cups with the lid liners removed.

Following animal preparation, glucose was injected into the intraperitoneal cavity. At 10, 20, 30, 60, 120, and 140 minutes blood glucose is sampled from the tail of each mouse by gently massaging a small drop of blood onto the glucometer strip. Glucose injections and blood glucose sampling is timed to take approximately the same amount of time per animal (i.e. 25 animals are injected in 12 minutes and blood glucose sampling of those same 25 animals should also take about 12 minutes) so that the sample times are accurate for each animal.

Fasting immunoreactive insulin levels: whole blood samples were spun in a refrigerated microfuge at 14,000 rpm for 10 minutes and transferred to a clean tube. 12 microliters of serum was tested using an ELISA assay (Crystal Chem) with mouse insulin as a standard according to the standard protocol that comes with the kit.

Reactive Oxygen Species (ROS) Formation Assay (Isolated Primary Hepatocytes)

Primary hepatocytes from diet-induced obese (DIO) and C57BL/6J mice were seeded in 12-well plates at a density of 2×105/well for 24 h. C57BL/6J hepatocytes were treated with 30 mM glucose in the absence or presence of GLP-1 (32-36)amide for 20 to 24 h and compared to DIO hepatocytes treated with GLP-1(32-36)amide. Cells were washed twice in HBSS (Hanks' Balance Salt Solution) and incubated with 10 uM 5-(and 6)-carboxy-2',7'-dichlorohydro-fluorescein diacetate (CM-H2DCFDA) for 45 minutes. The media were removed and cells were lysed. ROS was measured in the cell lysates using a spectrofluorometer (485 nm/535 nm). Data were normalized to values obtained from untreated controls.

Reactive Oxygen Species (ROS) Formation Assay (H4IIe Hepatoma Cells)

H4IIe cells were seeded in 12-well plates at a density of 1×104/well and incubated overnight in media containing 5.0 mM glucose. Media was then supplemented with 0.20 mM palmitate in BSA, with and without 100 pM GLP-1(32-36) amide and incubated for an additional 24 h. Intracellular ROS was measured by 5-(and 6)-carboxy-2',7'-dichloro-hydro-fluorescein diacetate (CM-H2DCFDA) (Molecular Probes) as follows. Cells were washed twice in HBSS (Hanks' Balance Salt Solution) and incubated with 10 uM CM-H2DCFDA for 45 minutes. The media were removed and cells were lysed. ROS was measured in the cell lysates using a spectrofluorometer (485 nm/535 nm). Data were normalized to values obtained from the cells treated with palmitate. BSA n=14. Palmitate n=13. 32-36/Palmitate n=12.

Statistical Analyses

The data are presented as the mean±SE. Statistical analysis was performed using Student's t-test. P values of less than 0.05 were considered statistically significant.

Results

GLP-1(32-36)Amide Attenuates Weight Gain in High Fat-Fed Mice.

Figure 1B:
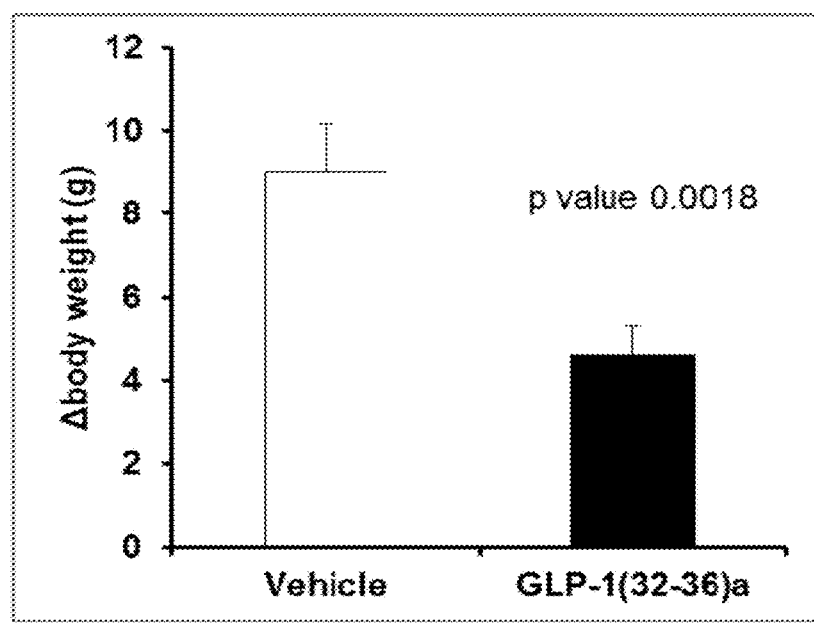

The continuous infusion of GLP-1(32-36)amide for fourteen weeks (31 weeks on the very high far diet) curtailed the rate of weight gain in mice fed VHFD (FIG. 1A). The inhibition of weight gain reached statistical significance by week five and it was maintained until the end of the twelve weeks of infusion. The body weight began to decrease at week 10 of the infusion of the pentapeptide corresponding to the leveling off of weight gain in the vehicle-treated control mice having reached a near maximum mean body weight of 50-55 gms for the C57bl/5 J mice on a high-fat diet [22, 23], The average weekly change in body weight gain of mice receiving peptide was 50% less than that of the mice receiving control vehicle, measured over ten weeks (FIG. 1B).

Figure 2A:
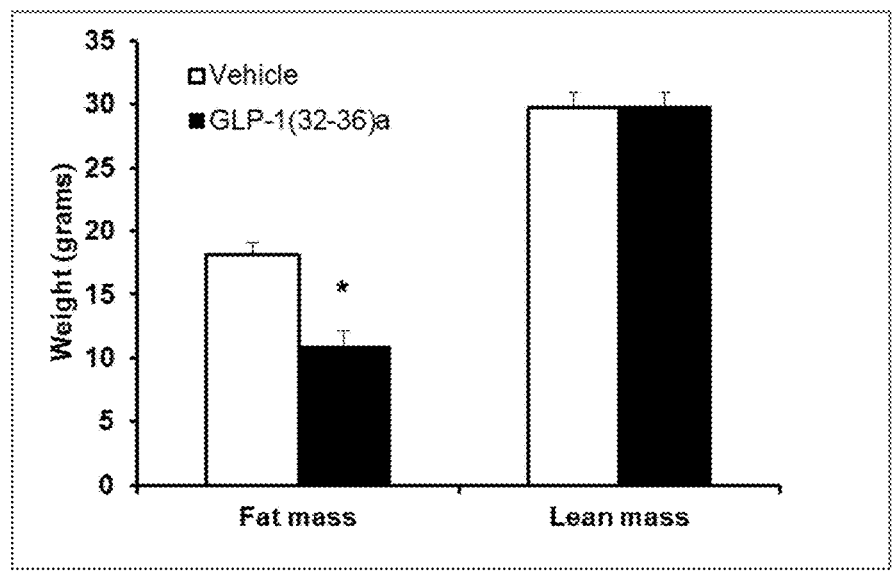
FIGS. 2A-D are bar graphs showing the results of determinations of lean, fat, and total body mass by dual X-ray absorptiometry (DXA) of mice receiving continuous infusions of the pentapeptide GLP-13(2-36)amide or control vehicle alone for 16 weeks. At the time of the study the mice were 39 weeks of age and on the very high fat diet for 33 weeks. 2A. Fat versus lean mass. The fat mass is 40% less in the pentapeptide infused compared to the control vehicle infused mice. *P<0.0008. There is no significant difference in the lean mass between the two groups of infused mice. 2B. Total body mass (lean+fat) differences in peptide infused versus vehicle control infused obese mice. *P<0.002. 2C. Fat mass expressed as the fraction of fat mass in peptide infused mice versus vehicle control infused obese mice. *P<0.0008. 2D. Fat mass expressed as the percentage of body weight, peptide-infused versus vehicle control-infused obese mice. *P<0.001. N=6 mice per group. Values are means+/−SEMs.
Figure 2B:
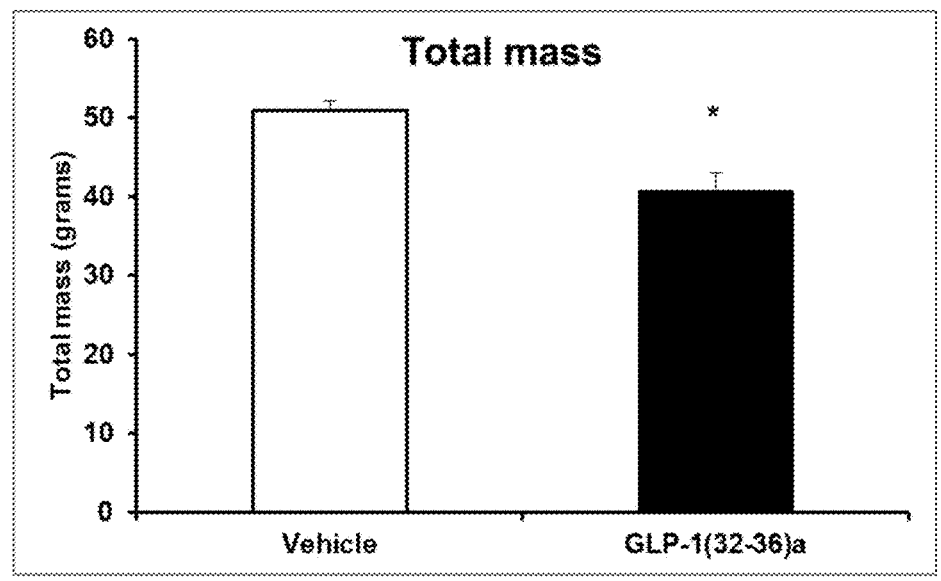
Figure 2C:
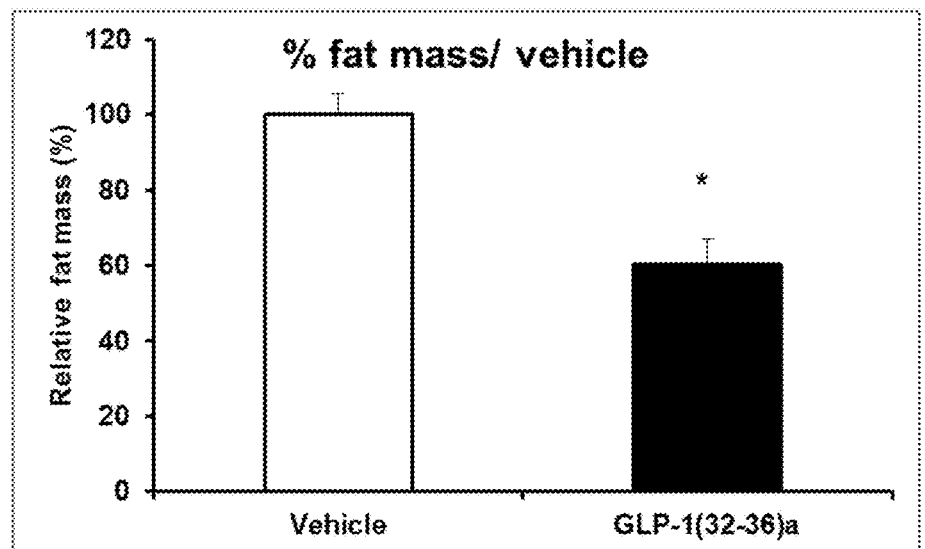
Figure 2D:
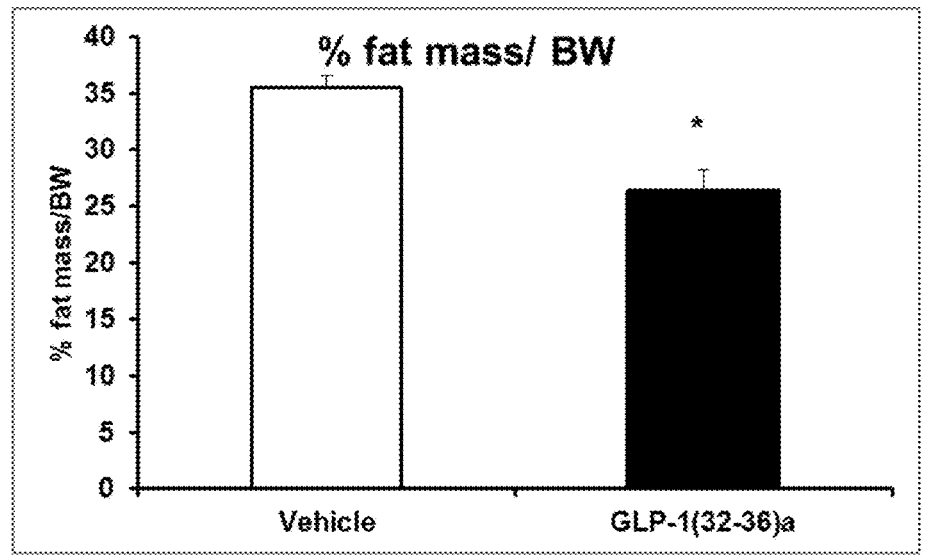

Measurements of body lean and fat mass by dual energy X-ray absorptiometry (DXA) immediately after week sixteen of the control vehicle and pentapeptide infusions showed a 40% reduction in fat mass in the peptide infused mice compared to control mice and no significant changes in lean mass (FIG. 2A). Infusion of the peptide also decreased total body mass (body weight) (FIG. 2B), the relative (%) fat mass compared to vehicle-treated mice (FIG. 2C), and the ratio of fat mass to body weight (FIG. 2D).

GLP-1(32-36)Amide Increases Energy Intake in VHFD-Fed Mice.

Figure 3:
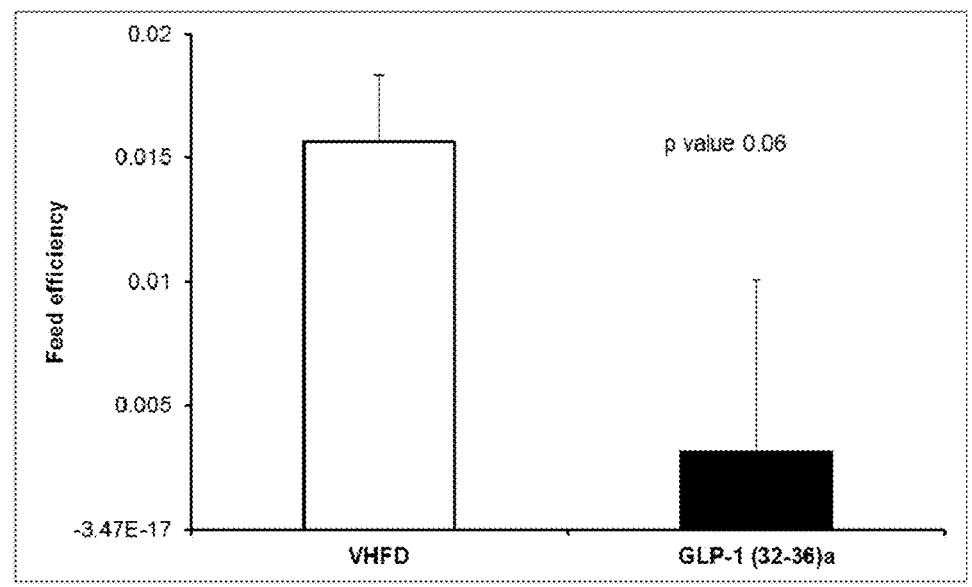
FIG. 3 is a bar graph showing feed efficiency at the end of 12 week infusion. GLP-1(32-36)amide infusions in diet-induced obese mice lowers the Feed Efficiency index. The data are the means+/−SEMs (*p<0.06 pentapeptide vs. vehicle) of the values calculated from the ten week period of infusions of control vehicle and GLP-1(32-36)amide shown in FIG. 4. The Feed efficiency (FE) is a calculation of the body weight (gms) divided by the energy intake kcal) in the food consumed. The lower FE in the mice receiving the pentapeptide GLP-1(32-36)amide compared to that of control vehicle indicates that less energy is going into weight and instead is expended. Basal energy expenditure in mice treated with pentapeptide is increased compared to mice treated with control vehicle. N=6 mice per group.

Measurements of food intake (energy intake) in the mice fed VHFD during ten weeks of infusion (weeks 2 to 10) reveals that the mice receiving the GLP-1(32-36)amide and vehicle infusions consume approximately the same number of calories: Vehicle, 1.11±0.025 Kcal/g body weight/week; GLP-1(32-36)amide, 1.15±0.030 Kcal/g body weight/week. The Feed Efficiency, an index of the caloric intake distributed into body weight, was decreased by approximately 50% in the peptide-infused obese mice compared to the control obese mice receiving infusion of vehicle alone (FIG. 3). These results suggest that a substantial proportion of the excessive energy intake was dissipated (burned) rather than going into body weight by the infusion of the peptide.

Figure 4A:
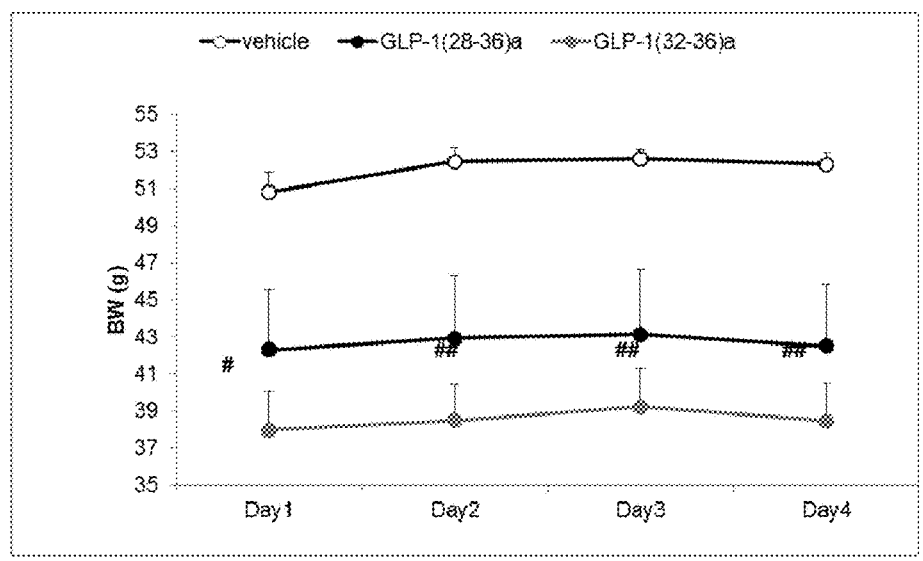
FIGS. 4A-C show the results of metabolic measurements of body weights, energy expenditure (VO2), and physical activities of mice during three days of monitoring in TSE-Systems metabolic cages. Mice were 37 weeks old and fed the very high fat diet for 31 weeks at the time of the study. 4A. Line graph showing body weights during three-day monitoring. Vehicle N=2; GLP-1s N=3. # p<0.01; ## p<0.006; ## p<0.008; ## p<0.007. 4B. Bar graph and line graph showing total body oxygen consumption (VO2) measured during both light and dark cycles for the three days of monitoring. Upper panel; Total VO2. Lower panel: Daily time-course of VO2 during light and dark cycles averaged over the three days. Vehicle N=2; GLP-1s N=3. 4C. Bar graph and line graph showing physical activity of the mice during the three days of the metabolic studies. Upper panel: Total activities averaged for light and dark cycles. Lower panel: Time-dependent measurements of activities. Activities were measured for hourly intervals during the light cycle of six hours (13:00 to 18:00) and for two hour intervals during the dark cycle of 12 hours (18:00 to 6:00). The differences in body weights and total VO2 were highly significant for GLP-1(32-36)amide versus control vehicle treated mice, whereas there were no significant differences in total activity between the two groups of mice (light cycle, p<0.4; dark cycle, N.S.). Vehicle N=2; GLP-1s N=3. The findings support a model of increased basal energy expenditure in mice infused with GLP-1(32-36)amide versus mice infused with control vehicle, independent of endogenous energy expenditure due to physical activity. N=3 mice for pentapeptide infusion and N=2 mice for control vehicle infusion.
Figure 4B:
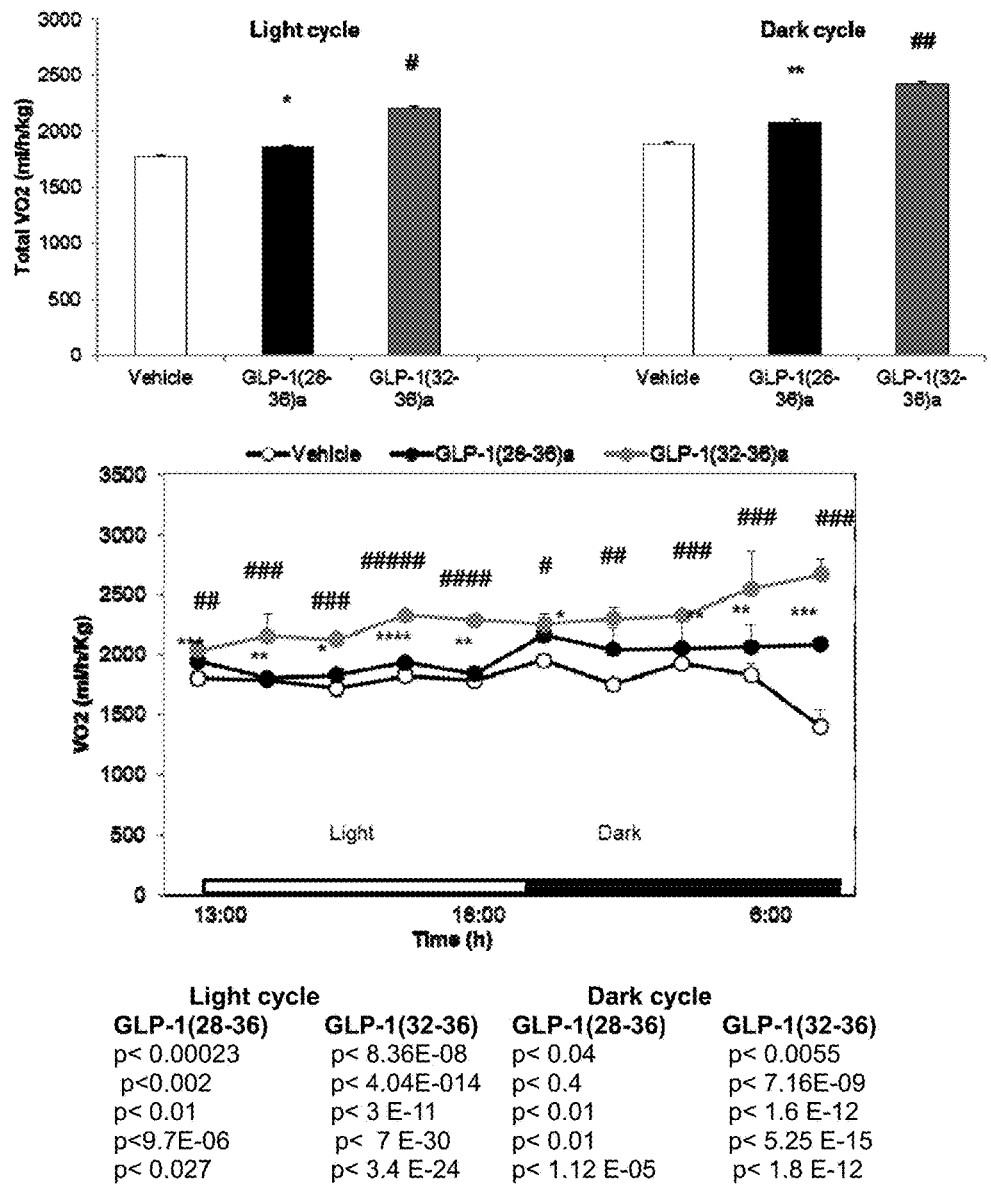
Figure 4C:
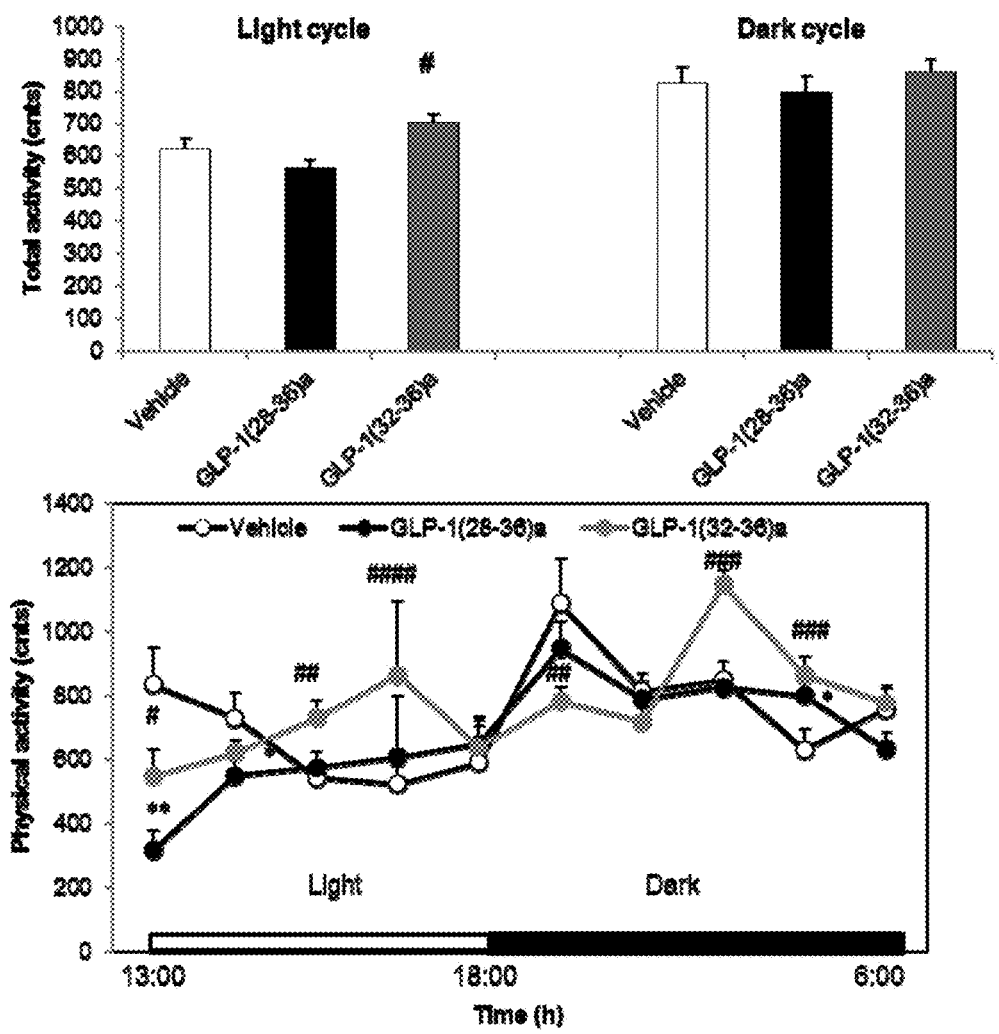
Figure 4D:
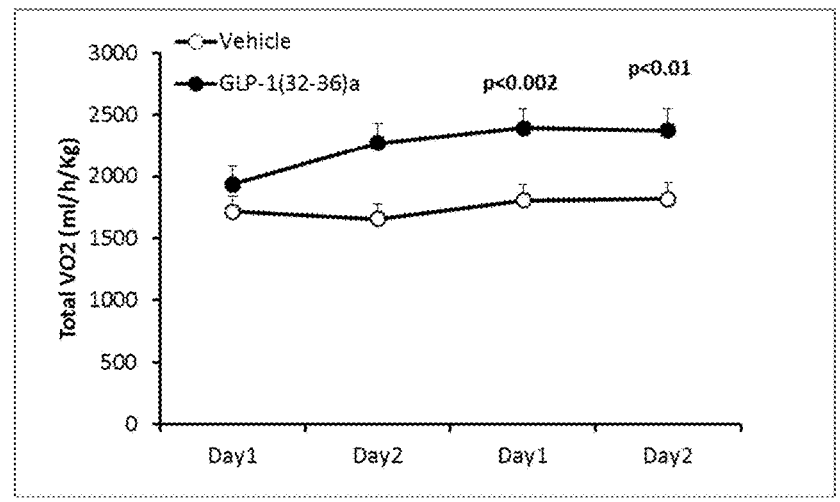
FIGS. 4D-G show the results of metabolic measurements of energy expenditure (VO2) of monitoring in TSE-Systems metabolic cages. Mice were 33-34 weeks old and fed the very high fat diet for 23-24 weeks at the time of the study. 4D and 4E. Line graph and bar graph showing total body oxygen consumption (VO2) measured during the light phase during two days. 4F and 4G. Line graph and bar graph showing lean body oxygen consumption (VO2) measured during the light phase during two days.
Figure 4E:
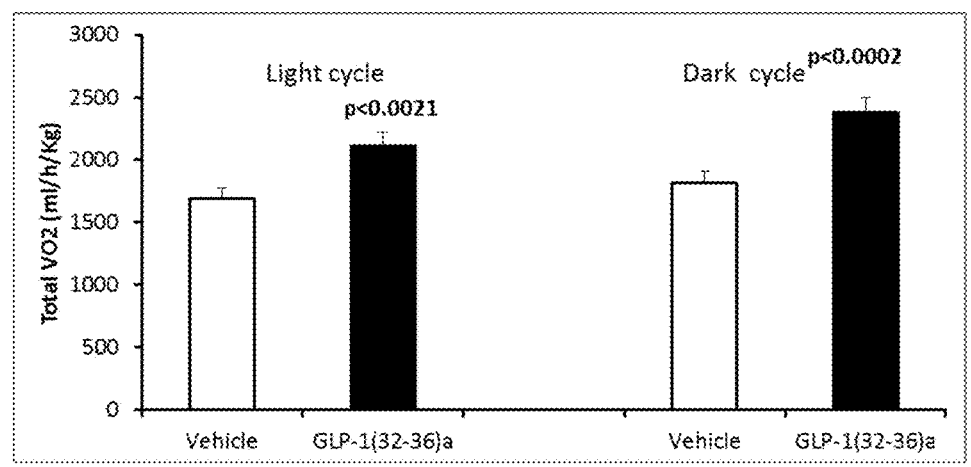
Figure 4F:
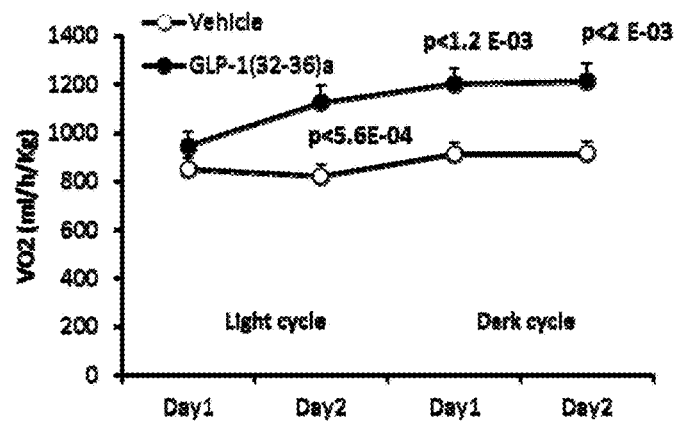
Figure 4G:
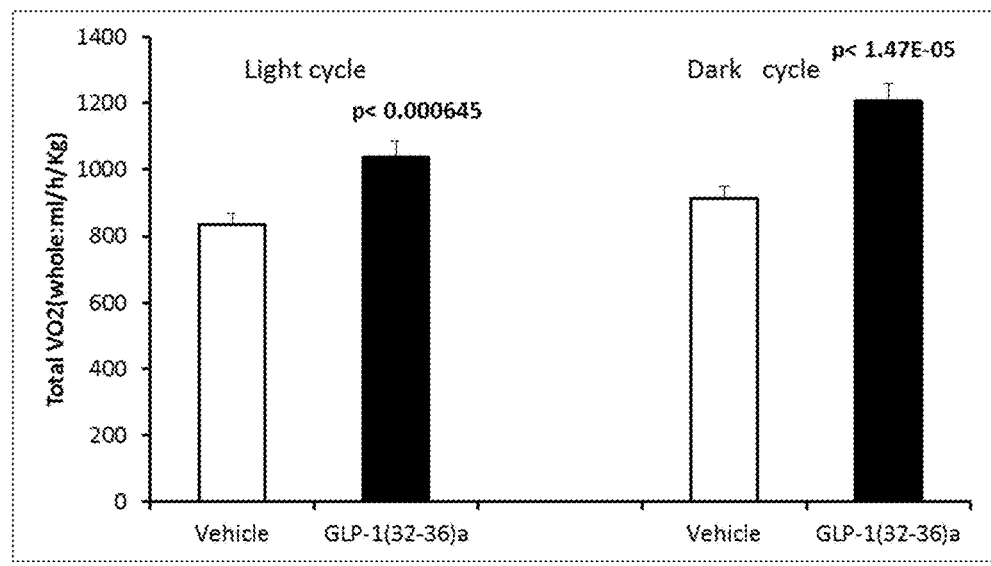

Analyses of Metabolic Parameters in a Closed System Shows that GLP-1(32-36)Amide Increases Basal Energy Expenditure Independently of Physical Activity Obese mice fed the VHFD for 31 weeks and receiving continuous infusions of GLP-1(32-36)amide or vehicle control for twelve weeks were monitored for three days in metabolic chambers. The mice were single caged. Parameters measured were body weight, oxygen consumption VO2, respiratory exchange rate, energy expenditure, home cage activity, drinking and feeding, and urine and feces production. The body weights held steady over the three days with vehicle-infused versus pentapeptide-infused mice averaging 52 grams and 38 grams, respectively (FIG. 4A). The whole body oxygen consumption (Total VO2) was significantly higher in the pentapeptide-infused mice compared to the control vehicle-infused mice for both the light cycle (P<5.9 E-43) and the dark cycle (P<4.0 E-66) (FIG. 4B). In addition, mice infused with GLP-1(32-36)amide showed an increase in resting oxygen consumption both during the light cycle (P<5.9 E-43) and the dark cycle (P<4.0 E-66) (Figure D and 4E). The average physical activities during both light and dark cycles were not significantly different between the mice receiving pentapeptide versus mice receiving control vehicle (FIG. 4C). Thus, the increase in VO2, a measure of energy expenditure was not due to changes in physical activity and is attributable to endogenous basal energy expenditure.

GLP-1(32-36)Amide Attenuates the Development of Fasting Hyperglycemia and Hyperinsulinemia and Insulin Resistance in High Fat Fed Mice.

Figure 5A:
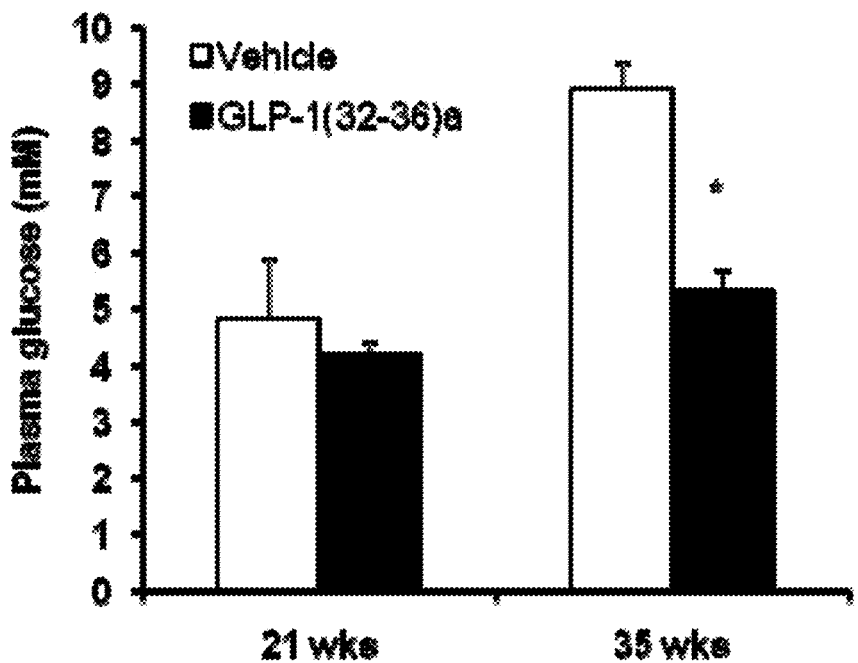
FIGS. 5A-B are a pair of bar graphs showing that GLP-1(32-36)amide attenuates the development of fasting hyperglycemia and hyperinsulinemia in high fat-fed mice. Mice fed the VHFD develop hyperglycemia, hyperinsulinemia, diabetes, and insulin resistance during weeks 15 to 29 of diet-induced obesity (21-35 weeks of age, respectively). A 12-week infusion of either control vehicle or pentapeptide started at 17 weeks on high-fat diet (23 weeks of age).
Figure 5B:
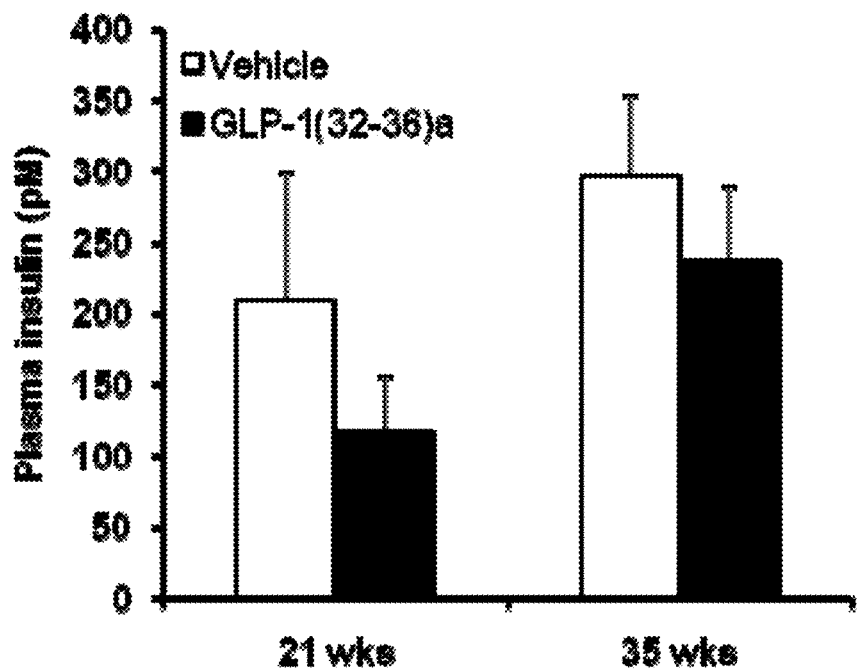
Figure 5C:
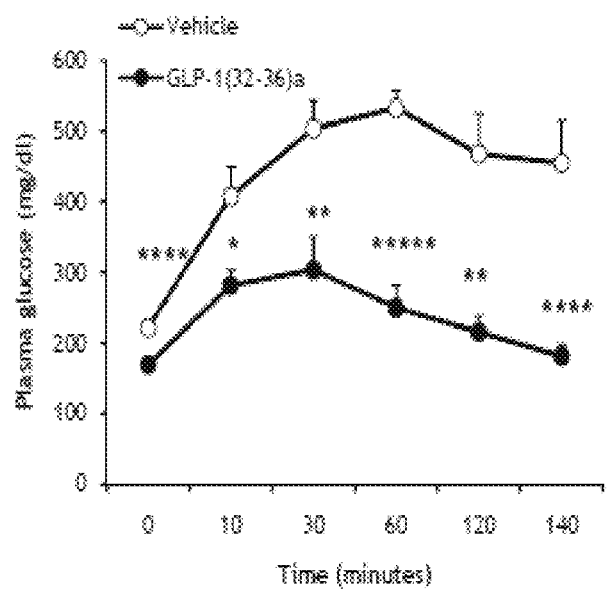
FIGS. 5C-D are a pair of line graphs Plasma glucose levels (FIG. 5C) and (FIG. 5D) Plasma insulin levels after an intraperitoneal glucose administration (2 mg/Kg BW ip) in overnight fasted mice fed in VHFD for 24-weeks and 16-weeks of continuous infusions of vehicle or GLP-1(32-36)amide. ***p<4E-03 vehicle vs. GLP-1(32-36)amide, *p<0.01 vehicle vs. GLP-1(32-36)amide, p<0.004 vehicle vs. GLP-1(32-36)amide, *p<1.7E-05 vehicle vs. GLP-1(32-36)amide, **p<6.7 E-04 vehicle vs. GLP-1(32-36) amide.
Figure 5D:
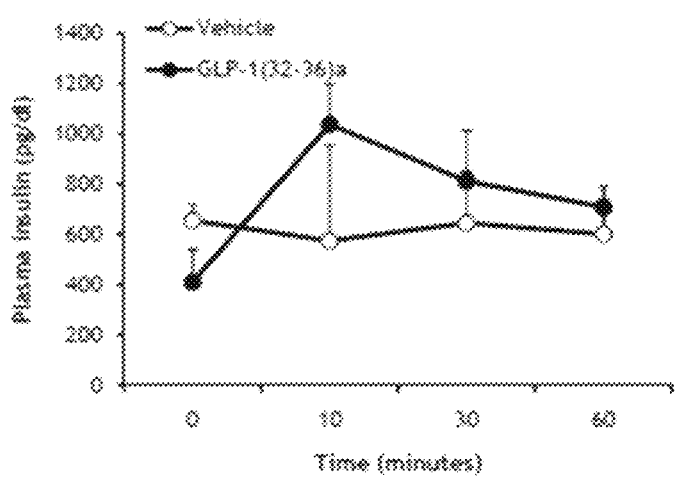

Fasting (16 hrs) plasma glucose and insulin levels were determined in the mice fed the high-fat diet (VHFD) for 15 weeks (21 weeks of age), two weeks before beginning the pentapeptide infusions, and again after 12 weeks of continuous infusion of the pentapeptide. at which time the mice were on the high-fat diet for 29 weeks (35 weeks of age). After 15 weeks on the high-fat diet both the plasma glucose and plasma insulin levels were elevated in both groups of mice; six mice destined to receive control vehicle infusions and six mice destined to receive infusions of the pentapeptide. Plasma glucose levels were 4 to 5 mM (normal range 3 to 4 mM) and plasma insulin levels were 120 to 200 pM (normal range 40 to 50 pM). By 29 weeks on diet (after 12 weeks of continuous infusion of control vehicle) the fasting plasma glucose and insulin levels increased to 8.8 mM and 300 pM, respectively. In contrast the mice receiving the continuous infusion of pentapeptide fasting plasma glucose levels were close to the normal range (5.5 mM) and plasma insulin levels were somewhat lower (250 pM), (FIGS. 5A and 5B) although not significantly different from the control vehicle level of 300 pM. The effectiveness of the pentapeptide infusion to lower fasting plasma glucose to the near normal range without an increase in plasma insulin levels indicates that the pentapeptide improved total body insulin sensitivity. Thus, the infusion of the pentapeptide in insulin-resistant diet-induced obese mice improves insulin sensitivity similar to the findings reported on the infusions of the 29 amino acid peptide, GLP-1[9-36)amide [16] and the nonapeptide, GLP-1(28-36)amide [17] in diet-induced obese, insulin-resistant mice. FIGS. 5C and 5D show plasma glucose (5C) and plasma insulin (5D) after an intraperitoneal glucose administration (2 mg/Kg BW ip) in overnight fasted mice fed in VHFD for 24-weeks and 16-weeks of continuous infusions of vehicle or GLP-1(32-36)amide, showing that GLP-1(28-36)amide treated mice have a normal glycemic response (5C) and a strong insulin response (5D), whereas the obese vehicle control mice have glucose intolerance and a loss of GSIS (glucose-stimulated Insulin secretion).

GLP-1(32-36)Amide Infusions Result in a Reduction of Triglyceride Accumulation in the Livers of High Fat Fed Mice.

Figure 6A:
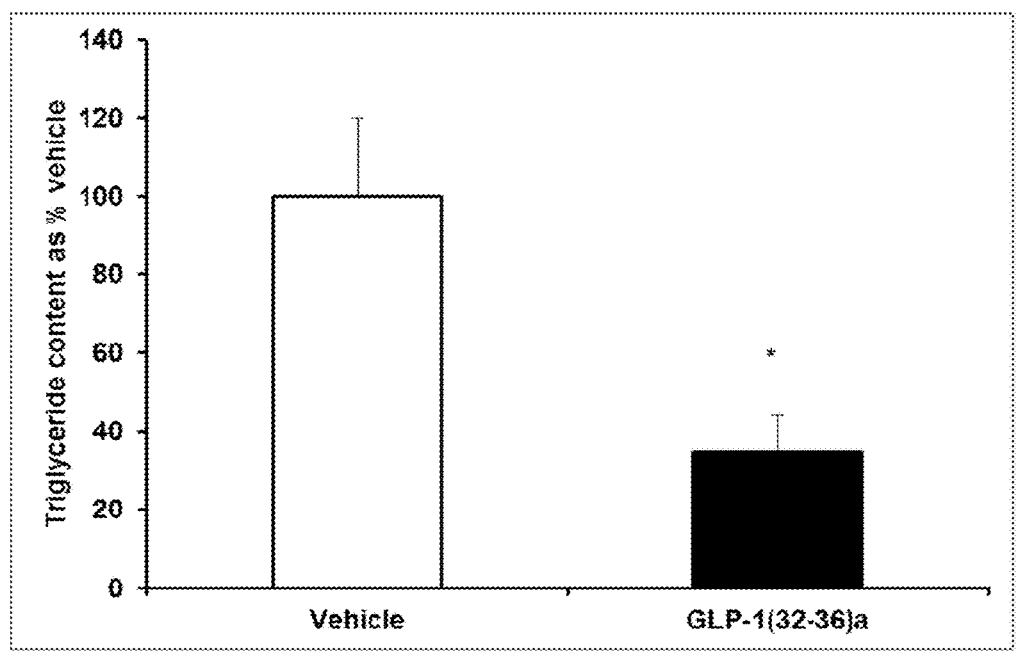
FIGS. 6A-B are bar graphs showing that infusions of GLP-1(32-36)amide in mice prevent the accumulation of triglyceride in the livers of mice fed a very high-diet (VHFD). Triglyceride contents of samples of livers of mice fed a high-fat diet (VHFD) for 32 weeks (age 38 weeks). 6A. Triglyceride levels of pentapeptide-infused obese mice as a percent of the vehicle-infused control mice set at 100%. *p<0.005. 6B. Triglyceride content levels of 60.5+/−12.1 mg/mg protein. Infusion of the pentapeptide lowered the triglyceride content by 65% to 21.1+/−5.6 mg/mg protein, indistinguishable from the values in the livers of lean mice fed low-fat chow (21.6+/−7 mg/mg protein). Data from diet-induced obese mice infused with the nonapeptide, GLP-1(28-36)amide for 16 weeks are also shown. Values are represented as % of vehicle control infused mice fed a high-fat diet (VHFD). *p<0.005, peptide vs. vehicle. N=6 mice per group. Values are means+/−SEMs.
Figure 6B:
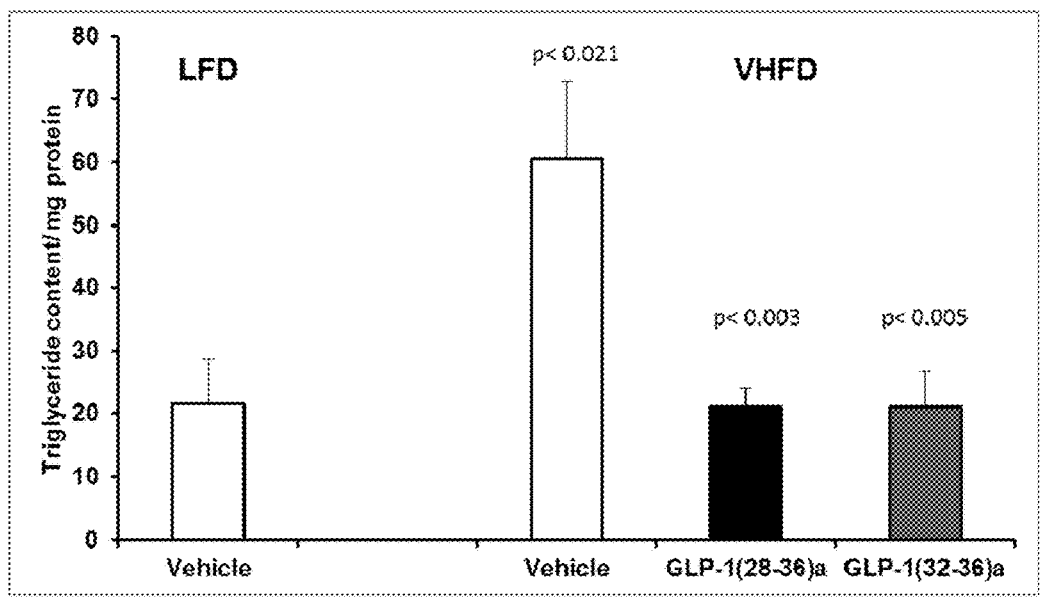

Livers from control mice fed a normal low-fat diet (LFD) and mice fed a high-fat diet (VHFD) infused with either GLP-1(32-36)amide or control vehicle alone were analyzed for contents of triglycerides. The mice receiving infusions of the pentapeptide were decreased by 65%; 35% of the vehicle control set at 100% (FIG. 6A) The livers of mice fed VHFD and received the control vehicle infusion had elevated triglyceride levels (60.5+/−12.1 mg/mg protein). The infusion of GLP-1(32-36)amide to mice fed the high-fat diet (VHFD) diminished the triglyceride accumulation by 65% to 21.1+/−5.6 mg/mg protein compared to control vehicle infusion, a reduction to that of the triglyceride content of normal mice fed a regular low fat diet (LFD (21.6+/−7) (FIG. 6B). FIG. 6C is a table showing continuous infusion of GLP-1(32-36)amide for 16-weeks improves plasma circulating levels of glycerol and triglyceride in mice fed on a 60% fat diet, called VHFD, very high-fat diet (Research Diets) for 24-weeks. $*p<0.02$, peptide vs. vehicle; $**p<0.008$ peptide vs. vehicle. Thus, GLP-1(32-36)amide improves lipid profile. GLP-1(32-36)amide prevents or reverses the first three of the manifestations of the metabolic syndrome, defined as obesity, diabetes, hyperlipidemia, and hypertension.

Mass Spectroscopy of Mouse Plasma Samples Indicate Rapid Conversion of GLP-1(9-36)Amide to the Nona and Pentapeptides by an Endopeptidase(s) in the Circulation.

Figure 7A:
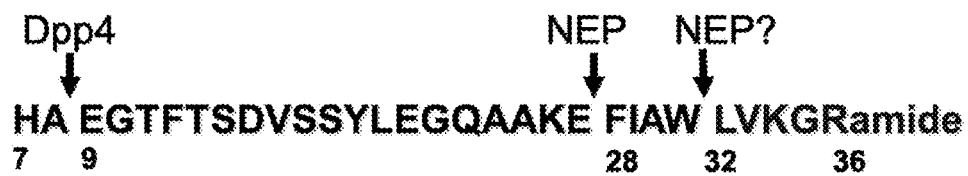
FIG. 7A is a diagram of the amino acid sequence of GLP-1(7-36)amide [HAEGTFTSDVSSYLEGQAAKEFI-AWLVKGRamide (SEQ ID NO:7)], the insulinotropic form of GLP-1 that augments glucose-sensitive insulin secretion, showing the sites cleaved by the two endopeptidases, Dpp4 and NEP. Dpp4 is a diaminopeptidyl peptidase that removes the first two amino acids of GLP-1, resulting in the formation of GLP-1(9-36)amide devoid of insulin-releasing activities and currently believed to be an inactive metabolite of GLP-1. This belief has become controversial since GLP-1(9-36)amide has been shown to have insulin-like actions on insulin responsive peripheral (extrapancreatic) tissues. [9-15] NEP, an abbreviation for NEP 24.11, is an endopeptidase, known as neprilysin, CALLA, CD10, that selectively cleaves on the amino-proximal side of hydrophobic amino acids such as the E-F site and the W-L site in GLP-1 generating the nonapeptide, GLP-1(28-36)amide [FI-AWLVKGRamide (SEQ ID NO:2)] and the pentapeptide, GLP-1(32-36)amide [LVKGRamide (SEQ ID NO:1)], respectively. The overwhelming current belief is that NEP completely degrades GLP-1 and is involved in its disposal [5, 6]. This belief is challenged by recent publications [17, 18] and the findings reported herein manuscript. The present results support the hypothesis that NEP is not a degrading enzyme for GLP-1. Rather the evidence supports the concept that NEP purposefully cleaves GLP-1, in particular the pro-peptide GLP-1(9-36)amide, to generate the two bioactive peptides, the pentapeptide and the nonapeptide, that have insulin-like and antioxidant-like actions on insulin resistant, stressed cells.
Figure 7B:
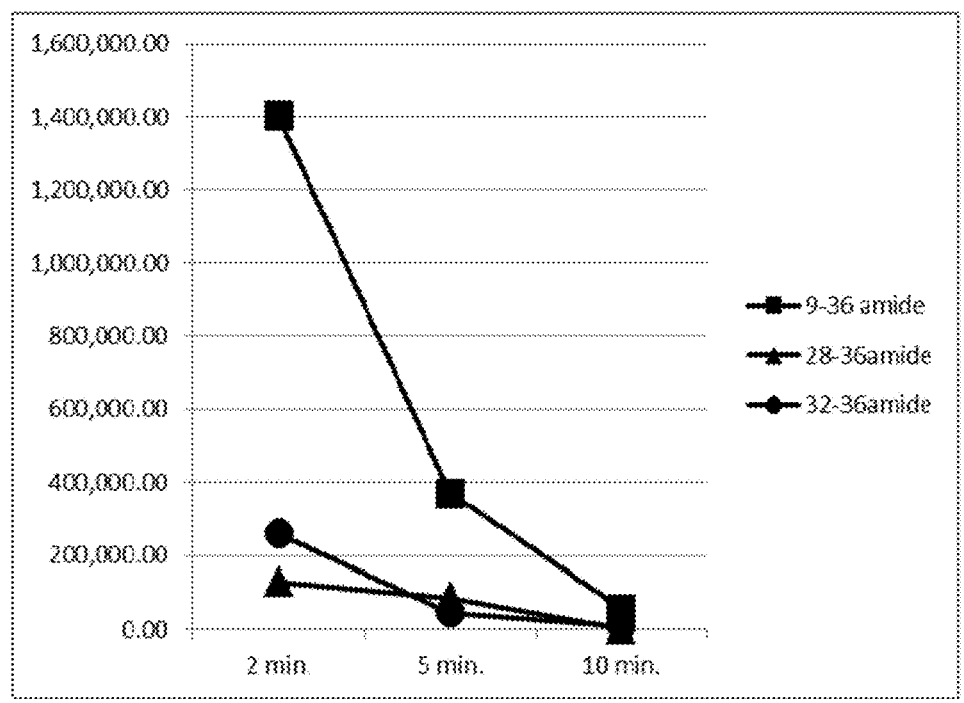
FIG. 7B is a line graph showing the results of experiments involving intravenous push injection of GLP-1(9-36)amide, 32-36 amide, and 38-36 amide into mice, collecting blood plasma at 2, 5, and 10 min, and analyzing the peptide profiles by liquid chromatography-mass spectrometry (LC-MS). Relative amounts of peptides at times indicated are shown. Y-axis, arbitrary units
Figure 7C:
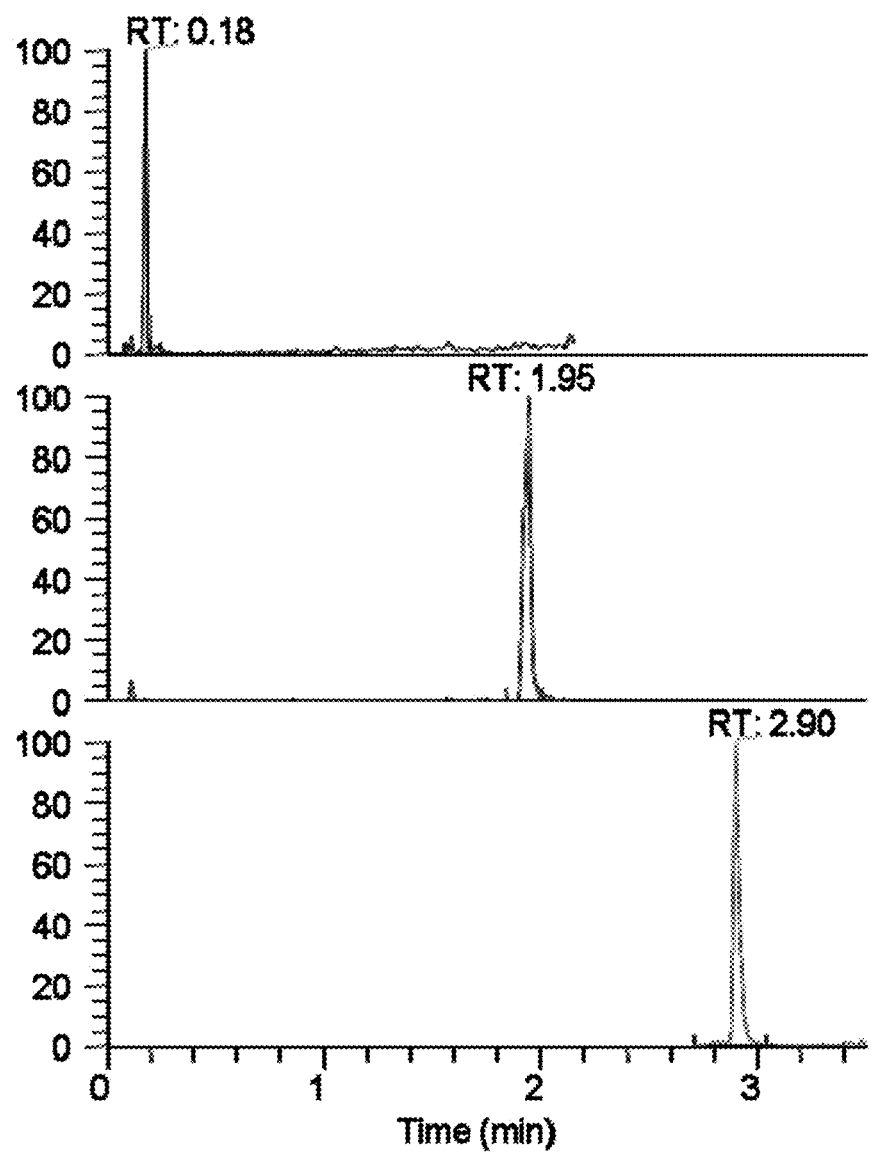
FIG. 7C shows data from LC-MS analyses of mouse plasma samples following i.v. injection of GLP-1(9-36) amide as described in FIG. 7B. The LC-MS profiles of the 2 min plasma sample shows the presence of the two peptides, 32-36 amide and 28-36 amide that could only have been generated by endopetididic cleavages from the GLP-1(9-36)amide pro-peptide that was injected into the mice.
Figure 8:
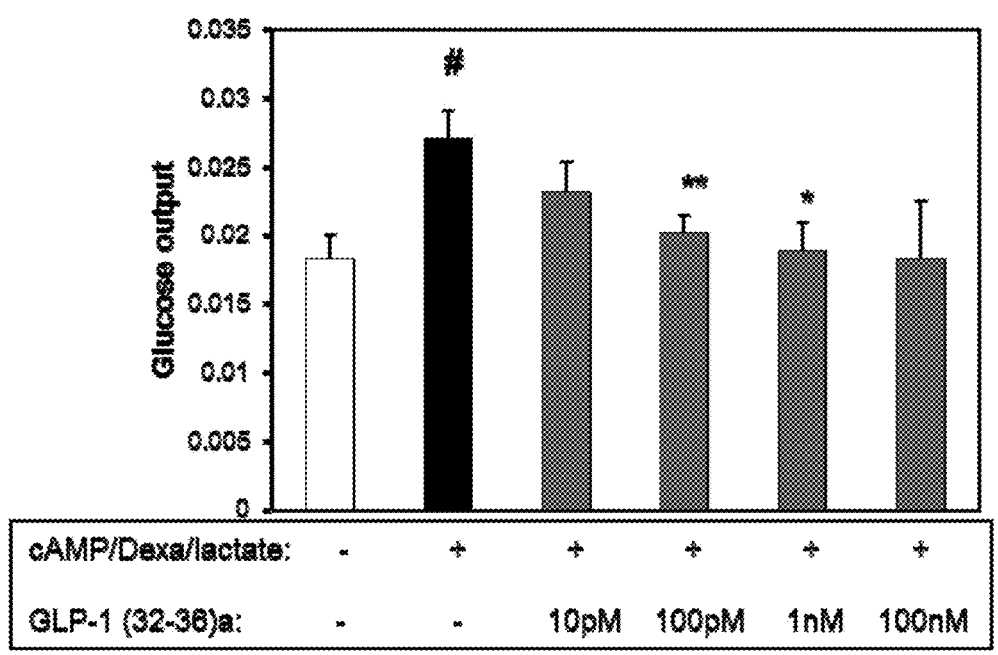
FIG. 8 is a bar graph showing suppression of glucose production by the pentapeptide GLP-1(32-36)amide (LVKGRamide (SEQ ID NO:1)) in insulin-resistant hepatocytes. Mice (male, C57bl/6) from 12-19 weeks of age were fasted overnight (16 hrs) and primary hepatocytes were isolated using a collagen and perfusion gradient purification [15]. Cells were first seeded using a Dulbecco's modified Eagle's medium (DMEM) supplemented with 10% FBS, 1 g/L glucose, 2 mmol/l sodium pyruvate, 1 micromol/L dexamethasone, and 0.1 micromol/L insulin, and later maintained in DMEM with 0.2% BSA, 1 g/L glucose, 0.1 micromol/L dexamethasone, and lnmol/L insulin. After an overnight incubation primary hepatocytes ($2\times10^5$ cells per well in twelve-well plates) were pre-treated with GLP-1(32-36) amide for 1 hour followed by stimulation with cAMP (100 microM)/dexamethasone (50 mM)/sodium lactate (2 mM) in glucose-free DMEM without phenol red containing the same concentrations of pentapeptide. After 2.5 hrs the culture media were collected for measuring glucose concentration with a colorimetric glucose assay kit (Sigma). The readings were then normalized to total protein content determined from whole-cell lysates. The data shown are the means+/− SEMs of three separate hepatocyte isolations.

To determine whether the nona and pentapeptides derived-from the C-terminus of GLP-1 are formed in the circulation of mice the propeptide GLP-1(9-36)amide, a product of the cleavage of the parent GLP-1 peptide, GLP-1(7-36)amide, by the diaminopeptidyl peptidase Dpp4, the GLP-1(9-36)amide was pulse-injected intravenously in mice. Plasma samples taken at 2 min after the injections were analyzed by electron spray mass spectrometry for the presence of the nona and pentapeptides (FIGS. 7B & C). Both peptides were readily detected in the plasma of mice injected with GLP-1(9-36)amide and not in the plasma of sham injected mice (FIG. 7C). These findings support the notion that GLP-1(9-36)amide, the major currently known circulating form of GLP-1, is rapidly converted to the nona and pentapeptides. Since it is known that the endopeptidase neprilysin (NEP 24.11) cleaves GLP-1 at sites between amino acids E27 and F28, and between W31 and L32 [7] (FIG. 7A), it seems reasonable to assume that the rapid appearance of the nona and pentapeptides in the circulation of mice by 2 min after the injection of GLP-1(9-36)amide occurs by the cleavages of GLP-1(9-36)amide. Further it seems reasonable to assume that the cleavages occur via the endopeptidase NEP 24.11, an enzyme known to exist in the circulations of mice and humans [24].

The plasma concentrations achieved during the continuous infusions of GLP-1(9-36)amide and GLP-1(28-36) amide were also determined by LC-MS. Plasma samples were pooled from terminal mice after four weeks of continuous infusions of peptides. GLP-1(9-36)amide was not detectable. However, the levels of GLP-1(28-36)amide in the mice infused with GLP-1(9-36)amide were ~100 pM and the mice infused with GLP-1(28-36)amide, at a concentration of 2.0 mg/ml in the osmopump, had plasma levels of ~240 pM. Thus plasma levels of the penta and nonapeptides achieved during the infusions of either GLP-1(9-36) made or GLP-1(28-36)amide were in the range of 100 pM to 240 pM. Since the normal circulating concentrations of total GLP-1 in the circulation, ~80% of which is GLP-1(9-36)amide, is 20-100 pM, the levels of nonapeptide achieved in the continuous infusion experiments are only modestly super-physiologic.

GLP-1(32-36)Amide Inhibits Glucose Production in Isolated Mouse Hepatocytes.

Figure 9A:
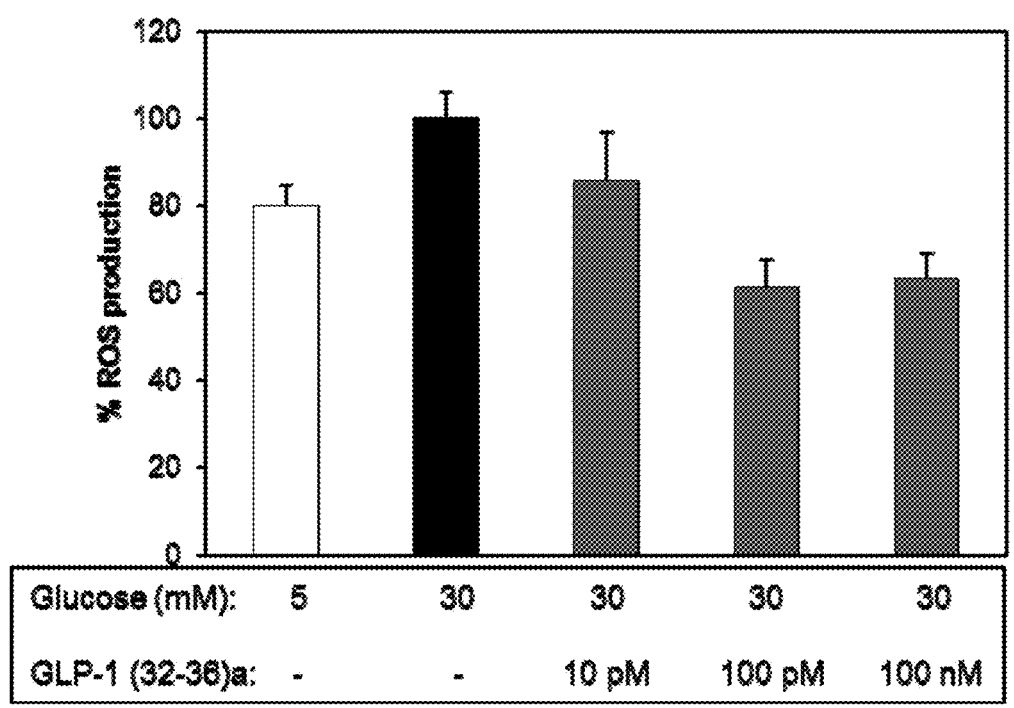
FIG. 9A is a bar graph showing suppression of the production of reactive oxygen species (ROS) by the pentapeptide GLP-1(32-36)amide in insulin-resistant isolated mouse hepatocytes. Hepatocytes were rendered insulin-resistant by their pre-incubation in 30 mM glucose. Primary hepatocytes from C57BL/6J mice were seeded at $2\times10^5$ cell per well in twelve-well plates and treated for 24 h with 30 mM glucose in the absence of presence of GLP-1(32-36) amide (10 pM, 100 pM and 100 nM). To measure ROS levels cells were washed twice in HBSS (Hanks' Balance Salt Solution) and incubated with 10 uM 5-(and 6)-carboxy-2',7'-dichlorohydro-fluorescein diacetate (CM-$H_2$DCFDA) (Molecular Probes) for 45 minutes. The media were removed and cells were lysed. ROS was measured in the cell lysates using a spectrofluorometer (485 nm/535 nm). Data were normalized to values obtained from untreated controls. The data shown are the means of two independent hepatocyte isolations+/−SEMs.

To determine whether there may be effects of GLP-1(32-36)amide on mitochondrial functions of oxidative phosphorylation in hepatocytes, gluconeogenesis was examined because uncontrolled hepatic gluconeogensis is an important contributor to fasting hyperglycemia in insulin-resistant diabetic individuals. Gluconeogenesis was stimulated in the isolated mouse hepatocytes by the addition of cAMP, dexamethasone, and lactate as described earlier [15]. The combination of cAMP, dexamethasone, and lactate induces insulin resistance in hepatocytes [25]. The addition of GLP-1 (28-36)amide to the hepatocytes dose-dependently suppressed glucose formation (FIG. 9A). Notably, suppression of glucose production occurred only to the component of glucose production stimulated by cAMP, dexamethasone and lactate, and not the basal glucose production, suggesting that the effects of GLP-1 in the suppression of hepatocyte glucose production is specific for insulin resistance.

GLP-1(32-36)Amide Suppresses Oxidative Stress and ROS Formation in Isolated Mouse Hepatocytes.

Figure 9B:
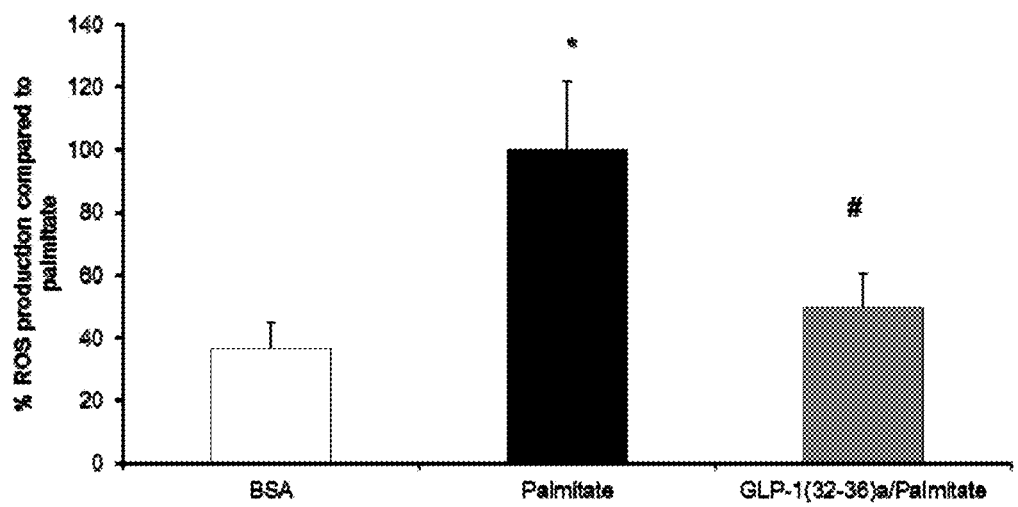
FIG. 9B is a bar graph showing inhibition of the production of ROS in H4IIe hepatoma cells. BSA n=14. palmitate n=13. 32-36/palmitate n=12. *p<0.005 palmitate vs BSA, # p<0.03 palmitate vs GLP-1(32-36)a/palmitate
Figure 10:
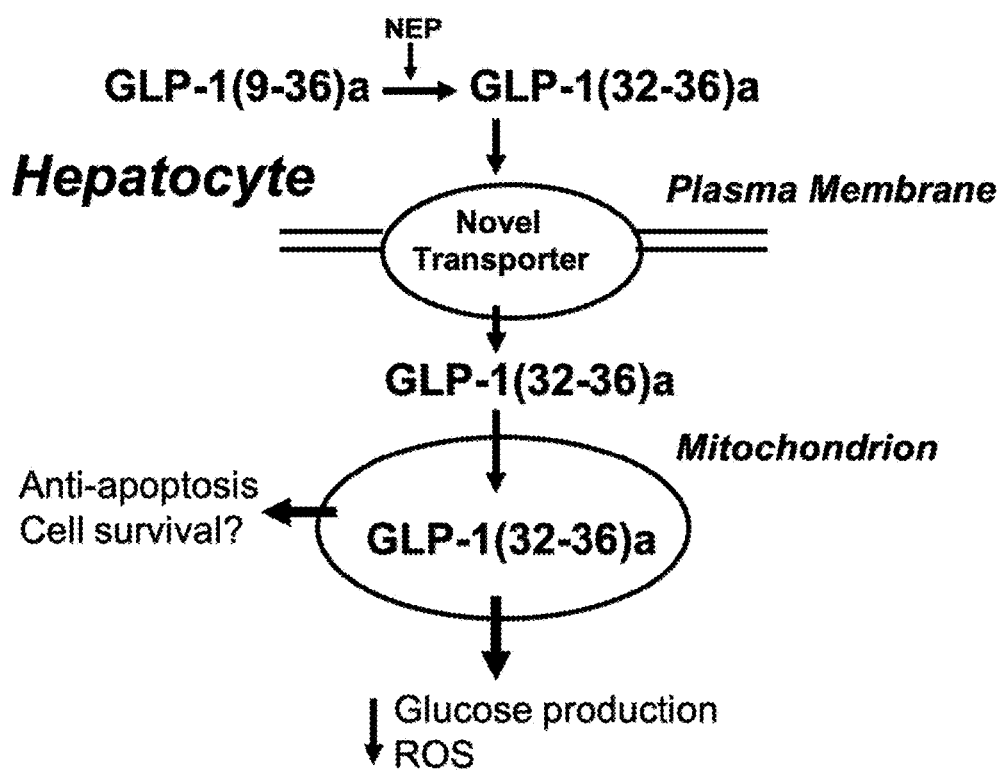
FIG. 10 is a schematic illustration of a hypothetical model of the proposed mechanism of GLP-1 action on hepatocytes. The mechanism proposed does not involve the known GLP-1 receptor. The major circulating form of GLP-1 are theorized to be GLP-1(32-36)amide and GLP-1(28-36) amide [8] formed by the cleavage of GLP-1(9-36)amide in the circulation by an endopeptidase such as NEP 24.11 or a related endopeptidase. The GLP-1(32-36)amide is transported into hepatocytes by an as yet unidentified mechanism such as by a novel receptor or transporter. After entry into the hepatocyte GLP-1(32-36)amide targets to mitochondria, gains access to the mitochondrial matrix, and modulates oxidative phosphorylation, gluconeogenesis, energy production, and cellular redox potential. It is proposed that the inhibition of oxidative stress by GLP-1(32-36)amide might have cytoprotective (anti-apoptosis) effects on hepatocytes.

Because the production of reactive oxygen species (ROS) by mitochondria is believed to be a major trigger for the development of insulin resistance [2], hepatic steatosis [1,26,27], and apoptosis via the stimulation of cytochrome C release and the activation of the caspase cascade [29], the intracellular levels of reactive oxygen species (ROS) were measured in hepatocytes in response to GLP-1(32-36)amide (FIGS. 9A and 9B). Hepatocytes isolated from the livers of normal mice were incubated in media containing 30 mM glucose to induce insulin resistance and oxidative stress (elevated levels of ROS). ROS levels were measured in hepatocytes using the fluorescent indicator CMH2DCFDA. The addition of GLP-1(32-36)amide ((10 pM, 100 pM and 100 nM) to the hepatocytes during their incubation in 30 mM glucose, which increased ROS levels, prevented the rise in ROS levels (FIG. 9A).

GLP-1(32-36)Amide Reduces ROS Production in Hepatoma Cells Treated with Palmitate.

FIG. 9B is a bar graph showing inhibition of the production of ROS in H4IIe hepatoma cells. H4IIe hepatoma cells were incubated with 0.2 mM palmitate in the presence or absence of GLP-1(32-36)amide for 24 hr. ROS production was measured in the whole cell lysate, $*p<0.005$ palmitate vs. BSA, $\#p<0.03$ palmitate vs GLP-1(32-36)a/Palmitate. FIG. 9B shows GLP-1(32-36)amide diminishes palmitate-induced oxidative stress. GLP-1(32-36)amide nearly completely normalizes the increase in cellular ROS levels induced by the fatty acid palmitate. The pentapeptide combats the excessive energy produced by fatty acid oxidation by uncoupling oxidative phosphorylation and converting the energy to heat and thereby prevents the energy from going into reactive oxygen species such as superoxides, which peroxidate mitochondrial proteins, damage them, elicit the SOS response (pre-apoptosis) and leads to the activation of the intrinsic apoptosis system, i.e., programmed cell death.

In summary, in a mouse model of diet-induced obesity and metabolic syndrome the pentapeptide LVKGRamide, GLP-1 (32-36)amide, curtails weight gain, increases basal energy expenditure, increases insulin sensitivity, prevents the development of glucose intolerance, diabetes, hyperlipidemia, and hepatic steatosis.

Type 2 diabetes is associated with hyperinsulinemia and insulin resistance leading to elevated hepatic glucose production, hyperglycemia, and hyperlipidemia. Infusions of the C-terminal pentapeptide LVKGRamide, GLP-1 (32-36) amide, derived from glucagon-like peptide-1 (GLP-1), in high fat diet-induced obese mice for sixteen weeks curtailed the rate of weight gain as early as five weeks. At the end of the sixteen week infusion, body weights of mice infused with GLP-1(32-36)amide were decreased by 50% compared to vehicle control that correlated with a 40% decrease in fat mass with no significant difference in lean mass. Indirect calorimetric studies showed that although mice infused with GLP-1(32-36)amide exhibited lower cumulative food consumption, the rate of oxygen consumption was significantly higher compared to vehicle control throughout the light and dark cycles, findings consistent with an increase in energy expenditure. These metabolic effects were not associated with changes in physical activity. Moreover, the infusion of GLP-1(32-36)amide for sixteen weeks in high fat-fed mice attenuated the development of diabetes since both plasma glucose and insulin were decreased close to values obtained in mice fed a control diet. Intraperitoneal glucose tolerance tests on mice fed the high-fat diet infused with GLP-1(32-36)amide were normal compared to impaired glucose tolerance seen in vehicle control obese mice. Livers obtained from peptide-treated mice showed less steatosis that correlated with a 65% decrease in triglyceride accumulation, equivalent to triglyceride levels in control mice fed a low fat diet. Moreover, plasma triglyceride glycerol levels were lowered by treatment of the mice with GLP-1(32-36)amide. These findings demonstrate biological actions and a role for the C-terminal pentapeptide, GLP-1(32-36)amide, in the treatment and improvement of obesity-related diabetes, insulin resistance, hypertriglyceridemia, and hepatic steatosis.

REFERENCES

[1] Grattagliano I, Palmieri V O, Portincasa P, Moschetta A, Palasciano G. Oxidative stress-induced risk factors associated with the metabolic syndrome: a unifying hypothesis. J Nutr Biochem 2008; 19:491-504.

[2] Haas J T, Biddinger S B. Dissecting the role of insulin resistance in the metabolic syndrome. Curr Opin Lipidol 2009; 20:206-210.

[3] Lovshin, J A and Drucker, D J Incretin-based therapies for type 2 diabetes mellitus. Nat. Rev. Endocrinol. 2009; 5: 262-269.

[4] Kieffer, T J and Habener, J F. The glucagon-like peptides. Endocr Rev 1999; 20:876-913

[5] Plamboeck A, Hoist J J, Carr R D, Deacon C F. Neutral endopeptidase 24.11 and dipeptidyl peptidase IV are both involved in regulating the metabolic stability of glucagon-like peptide-1 in vivo. Adv Exp Med Biol. 2003; 524: 303-12.

[6] Deacon C F. Circulation and degradation of GIP and GLP-1. Horm. Metab. Res. 2004; 36:761-765.

[7] Hupe-Sodmann K, McGregor G P, Bridenbaugh R, GOke R, GOke B, Thole H, Zimmermann B, Voigt K. Characterisation of the processing by human neutral endopeptidase 24.11 of GLP-1(7-36) amide and comparison of the substrate specificity of the enzyme for other glucagon-like peptides. Regul Pept 1995; 58:149-156.

[8] Tomas E, Habener J F. Insulin-like actions of glucagon-like peptide-1: A dual receptor hypothesis. Trends Endocrinol Metab 2010; 2159-2167.

[9] Nikolaidis, L A, Elahi D, Shen, Y T, Shannon, R P. Active metabolite of GLP-1 mediates myocardial glucose uptake and improves left ventricular performance in conscious dogs with dilated cardiomyopathy. Am. J. Physiol. Heart Circ. Physiol. 2005; 289:H2401-H2408.

[10] Ban, K, Noyan-Ashraf, M H, Hoefer, J, Bolz, S S, Drucker, D J, Husain, M. Cardioprotective and vasodilatory actions of glucagon-like peptide 1 receptor are mediated through both glucagon-like peptide 1 receptor-dependent and receptor-independent pathways. Circulation 2008; 117:2340-2350.

[11] Sonne, D. P., Engstrom, T., Treiman, M. Protective effects of GLP-1 analogues exendin-4 and GLP-1(9-36) amide against ischemia-reperfusion injury in rat heart. Regul. Pept. 2008; 146: 243-249.

[12] Ban K, Kim K H, Cho C K, Sauvé M, Diamandis E P, Backx P H, Drucker D J, Husain M. Glucagon-like peptide (GLP)-1(9-36)amide-mediated cytoprotection is blocked by exendin(9-39) yet does not require the known GLP-1 receptor. Endocrinology. 2010; 151:1520-1531.

[13] Green, B D, Hand, K V, Dougan, J E, McDonnell, B M, Cassidy, R S, Grieve, D J. GLP-1 and related peptides cause concentration-dependent relaxation of rat aorta through a pathway involving KATP and cAMP. Arch. Biochem. Biophys, 2008; 478:136-142.

[14] Elahi, D, Egan, J M, Shannon, R P, Meneilly, G S, Khatri, A, Habener, J F, Andersen, D K. Glucagon-like peptide-1 (9-36) amide, cleavage product of glucagon-like peptide-1 (7-36) is a glucoregulatory peptide. Obesity 2008; 16:1501-1509.

[15] Tomas E, Stanojevic V, Habener J F. GLP-1(9-36)amide metabolite and suppression of glucose production in isolated mouse hepatocytes. Horm Metab Res 2010; 42:657-662.

[16] Tomas E, Stanojevic V, Wood J A, Habener J F. GLP-1(9-36)amide metabolite inhibits weight gain and attenuates diabetes and hepatic steatosis in diet-induced obese mice. Diabetes Obes Metab. 2011; 13:26-33.

[17] Tomas E, Wood J A, Stanojevic V, Habener J F. GLP-1-derived nonapeptide GLP-1(28-36)amide inhibits weight gain and attenuates diabetes and hepatic steatosis in diet-induced obese mice. Regul Pept. 2011; 169:43-48

[18] Tomas E, Stanojevic V, Habener, J F. GLP-1-Derived Nonapeptide GLP-1(28-36)amide targets to mitochondria and suppresses glucose production and oxidative stress in isolated mouse hepatocytes. Regul Pept 2011; 167:177-184.

[19] Abu-Hamdah, R, Rabiee, A, Meneilly, G S, Shannon, R P, Andersen, D K, Elahi D. Clinical review: The extrapancreatic effects of glucagon-like peptide-1 and related peptides. J. Clin. Endocrinol Metab. 2009; 94:1843-1852.

[20] Zhang J, Tokui Y, Yamagata K, Kozawa J, Sayama K, Iwahashi H, Okita K, Miuchi M, Konya H, Hamaguchi T, Namba M, Shimomura I, Miyagawa J I. Continuous stimulation of human glucagon-like peptide-1 (7-36) amide in a mouse model (NOD) delays onset of autoimmune type 1 diabetes. Diabetologia. 2007; 50:1900-1999.

[21] Parekh P I, Petro A E, Tiller J M, Feinglos M N, Surwit R S. Reversal of diet-induced obesity and diabetes in C57BL/6J mice. Metabolism. 1998; 47:1089-1096.

[22] Bartels E D, Bang C A, Nielsen L B. Early atherosclerosis and vascular inflammation in mice with diet-induced type 2 diabetes. Eur J Clin Invest. 2009 March; 39(3): 190-9.

[23] Guo J, Jou W, Gavrilova O, Hall K D Persistent diet-induced obesity in male C57BL/6 mice resulting from temporary obesigenic diets. PLoS One. 2009; 4(4): e5370.

[20] Standeven K F, Hess K, Carter A M, Rice G I, Cordell P A, Balmforth A J, Lu B, Scott D J, Turner A J, Hooper N M, Grant P J. Neprilysin, obesity and the metabolic syndrome. Int J Obes (Lond). 2010 Nov. 2.

[25] Liu H Y, Collins Q F, Xiong Y, Moukdar F, Lupo E G Jr, Liu Z, Cao W. Prolonged treatment of primary hepatocytes with oleate induces insulin resistance through p38 mitogen-activated protein kinase. J Biol Chem. 2007 May 11; 282:14205-14212.

[26] Watanabe S, Yaginuma R, Ikejima K, Miyazaki A. Liver diseases and metabolic syndrome. J Gastroenterol. 2008; 43:509-518.

[27] Stein L L, Dong M H, Loomba R. Insulin sensitizers in nonalcoholic fatty liver disease and steatohepatitis: Current status. Insulin sensitizers in nonalcoholic fatty liver disease and steatohepatitis: Current status. Adv Ther 2009; 26:893-907.

[28] Reddy J K, Rao M S. Lipid metabolism and liver inflammation. II. Fatty liver disease and fatty acid oxidation. Am J Physiol Gastrointest Liver Physiol. 2006; 290:G852-8.

[29] Zhao K, Zhao G M, Wu D, Soong Y, Birk A V, Schiller P W, Szeto H H. Cell-permeable peptide antioxidants targeted to inner mitochondrial membrane inhibit mitochondrial swelling, oxidative cell death, and reperfusion injury. J Biol Chem. 2004; 13; 279:34682-34690.

[30] Plamboeck, A., Holst, J. J., Carr, R. D., Deacon, C. F. Neutral endopeptidase 24.11 and dipeptidyl peptidase IV are both mediators of the degradation of glucagon-like peptide 1 in the anaesthetized pig. Diabetologia 2005; 48:1882-1890.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating obesity, metabolic syndrome, hepatic steatosis, non-hepatic steatosis, hypertriglyceridemia, or diabetes in a subject, the method comprising administering a therapeutically effective amount of a composition comprising an isolated peptide consisting of a sequence (SEQ ID NO: 3)
Leu-Val-(Lys/Arg)-Gly-Arg-Xaa, wherein Xaa can be Gly, Gly-Arg, Gly-Arg-Gly, or absent, and a physiologically acceptable carrier, to a subject in need thereof.

2. The method of claim 1, wherein the subject is obese.

3. The method of claim 1, wherein the subject is obese due to consumption of a high fat diet.

4. The method of claim 1, wherein the C terminus of the isolated peptide is an Arg and the peptide is amidated.

5. The method of claim 1, wherein one or more amino acids of the isolated peptide are modified by attachment of a fatty acid.

6. The method of claim 5, wherein the fatty acid is selected from the group consisting of palmitate and oleate.

7. The method of claim 1, wherein Xaa is absent.

8. The method of claim 1, wherein Xaa is Gly.

9. The method of claim 1, wherein Xaa is Gly-Arg.

10. The method of claim 1, wherein Xaa is Gly-Arg-Gly.

11. The method of claim 1, wherein the isolated peptide is fused to a cell-penetrating peptide.

12. The method of claim 11, wherein the cell-penetrating peptide is fused on the C-terminus of the peptide of SEQ ID NO:3.

13. The method of claim 11, wherein the cell-penetrating peptide is selected from the group consisting of HIV-derived TAT peptide, penetratins, transportans, SS peptides, and hCT derived cell-penetrating peptides.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: GLP-1 derived artificial peptide

<400> SEQUENCE: 1

Leu Val Lys Gly Arg
 1               5

<210> SEQ ID NO 2
<211> LENGTH: 9
<212> TYPE: PRT
<213> ORGANISM: Artificial Sequence
<220> FEATURE:
<223> OTHER INFORMATION: GLP-1 derived artificial peptide

<400> SEQUENCE: 2

Phe Ile Ala Trp Leu Val Lys Gly Arg
 1               5

<210> SEQ ID NO 3
<211> LENGTH: 8
<212> TYPE: PRT
<213> ORGANISM: Artificial Sequence
<220> FEATURE:
<223> OTHER INFORMATION: GLP-1 derived artificial peptide
<220> FEATURE:
<221> NAME/KEY: VARIANT
<222> LOCATION: 3
<223> OTHER INFORMATION: Xaa = K or R
<220> FEATURE:
<221> NAME/KEY: VARIANT
<222> LOCATION: 6
<223> OTHER INFORMATION: Xaa = G or absent
```

```
<220> FEATURE:
<221> NAME/KEY: VARIANT
<222> LOCATION: 7
<223> OTHER INFORMATION: Xaa = R or absent
<220> FEATURE:
<221> NAME/KEY: VARIANT
<222> LOCATION: 8
<223> OTHER INFORMATION: Xaa = G or absent

<400> SEQUENCE: 3

Leu Val Xaa Gly Arg Xaa Xaa Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: GLP-1 derived artificial peptide

<400> SEQUENCE: 4

Leu Val Lys Gly Arg Gly
 1               5

<210> SEQ ID NO 5
<211> LENGTH: 6
<212> TYPE: PRT
<213> ORGANISM: Artificial Sequence
<220> FEATURE:
<223> OTHER INFORMATION: GLP-1 derived artificial peptide

<400> SEQUENCE: 5

Leu Val Arg Gly Arg Gly
 1               5

<210> SEQ ID NO 6
<211> LENGTH: 5
<212> TYPE: PRT
<213> ORGANISM: Artificial Sequence
<220> FEATURE:
<223> OTHER INFORMATION: GLP-1 derived artificial peptide

<400> SEQUENCE: 6

Leu Val Arg Gly Arg
 1               5

<210> SEQ ID NO 7
<211> LENGTH: 30
<212> TYPE: PRT
<213> ORGANISM: Artificial Sequence
<220> FEATURE:
<223> OTHER INFORMATION: GLP-1 derived artificial peptide

<400> SEQUENCE: 7

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
             20                  25                  30

<210> SEQ ID NO 8
<211> LENGTH: 5
<212> TYPE: PRT
<213> ORGANISM: Artificial Sequence
<220> FEATURE:
<223> OTHER INFORMATION: GLP-1 derived artificial peptide

<400> SEQUENCE: 8
```

```
Arg Gly Lys Val Leu
1               5

<210> SEQ ID NO 9
<211> LENGTH: 6
<212> TYPE: PRT
<213> ORGANISM: Artificial Sequence
<220> FEATURE:
<223> OTHER INFORMATION: GLP-1 derived artificial peptide

<400> SEQUENCE: 9

Gly Arg Gly Lys Val Leu
1               5

<210> SEQ ID NO 10
<211> LENGTH: 7
<212> TYPE: PRT
<213> ORGANISM: Artificial Sequence
<220> FEATURE:
<223> OTHER INFORMATION: GLP-1 derived artificial peptide

<400> SEQUENCE: 10

Arg Gly Arg Gly Lys Val Leu
1               5
```